(12) United States Patent
Honda et al.

(10) Patent No.: US 8,740,780 B2
(45) Date of Patent: Jun. 3, 2014

(54) ENDOSCOPE AND ILLUMINATION APPARATUS FOR ENDOSCOPE

(71) Applicants: Olympus Medical Systems Corp., Tokyo (JP); Olympus Corporation, Tokyo (JP)

(72) Inventors: Kazuki Honda, Higashiyamato (JP); Sho Shinji, Hachioji (JP); Yuichi Ikeda, Tama (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 0 days.

(21) Appl. No.: 13/650,369

(22) Filed: Oct. 12, 2012

(65) Prior Publication Data

US 2013/0137923 A1    May 30, 2013

Related U.S. Application Data

(63) Continuation of application No. PCT/JP2012/058967, filed on Apr. 2, 2012.

(30) Foreign Application Priority Data

Apr. 7, 2011  (JP) ................. 2011-085315
Nov. 10, 2011 (JP) ................. 2011-246739

(51) Int. Cl.
*A61B 1/06* (2006.01)
*A61B 1/00* (2006.01)

(52) U.S. Cl.
CPC ............. *A61B 1/0607* (2013.01); *A61B 1/0615* (2013.01); *A61B 1/00177* (2013.01)
USPC ............ 600/177; 600/170; 600/182; 362/574

(58) Field of Classification Search
CPC ...................................................... A61B 1/0607
USPC ............... 600/182, 177, 178, 170; 362/23.16, 362/574, 572, 602, 609, 610; 385/901
See application file for complete search history.

(56) References Cited

U.S. PATENT DOCUMENTS 4,403,273 A * 9/1983 Nishioka ........................ 362/574
4,671,630 A * 6/1987 Takahashi ..................... 359/503
(Continued)

FOREIGN PATENT DOCUMENTS

JP       62-13284  Y2   4/1987
JP       11-76148  A    3/1999
(Continued)

*Primary Examiner* — John P Leubecker
(74) *Attorney, Agent, or Firm* — Scully, Scott, Murphy & Presser, P.C.

(57) ABSTRACT

An illumination apparatus for an endoscope guiding externally-entering light to a transparent light-guiding body including an annular-shaped annular portion, the annular portion including inner and outer circumferential faces, and making the light exit from the annular portion as illuminating light, wherein the light-guiding body includes: a notch portion formed by cutting out a part of the annular portion so as to form a line extending perpendicularly from the outer circumferential face toward the inner circumference side of the annular portion from a line extending from a point on an outer circumference of a circle in a cross section of the annular portion; and an incident portion that allows the light to enter in a direction along the line extending from the point on the outer circumference, the direction being a direction perpendicular to a cutout surface of the notch portion provided in the annular portion.

18 Claims, 32 Drawing Sheets

(56) References Cited

U.S. PATENT DOCUMENTS

| | | | |
|---|---|---|---|
| 5,591,192 A * | 1/1997 | Privitera et al. | 606/185 |
| 7,500,774 B2 * | 3/2009 | Nishiyama et al. | 362/551 |
| 7,553,037 B2 * | 6/2009 | Sullivan | 362/26 |
| 7,654,679 B2 * | 2/2010 | Mezouari | 362/23 |
| 7,959,651 B2 * | 6/2011 | Branch et al. | 606/245 |
| 8,016,441 B2 * | 9/2011 | Birman et al. | 362/26 |
| 8,343,043 B2 * | 1/2013 | Kase et al. | 600/176 |
| 2004/0066659 A1 * | 4/2004 | Mezei et al. | 362/555 |
| 2006/0139946 A1 * | 6/2006 | Tamaki | 362/602 |
| 2006/0268570 A1 | 11/2006 | Vayser et al. | |
| 2007/0159846 A1 * | 7/2007 | Nishiyama et al. | 362/602 |
| 2008/0269563 A1 * | 10/2008 | Takahashi | 600/178 |
| 2009/0076329 A1 * | 3/2009 | Su et al. | 600/134 |
| 2011/0201889 A1 * | 8/2011 | Vayser et al. | 600/182 |

FOREIGN PATENT DOCUMENTS

| | | |
|---|---|---|
| JP | 2008-155016 A | 7/2008 |
| JP | 2008-534237 A | 8/2008 |
| JP | 2010-194191 A | 9/2010 |
| WO | WO 2006/108143 A2 | 10/2006 |

* cited by examiner

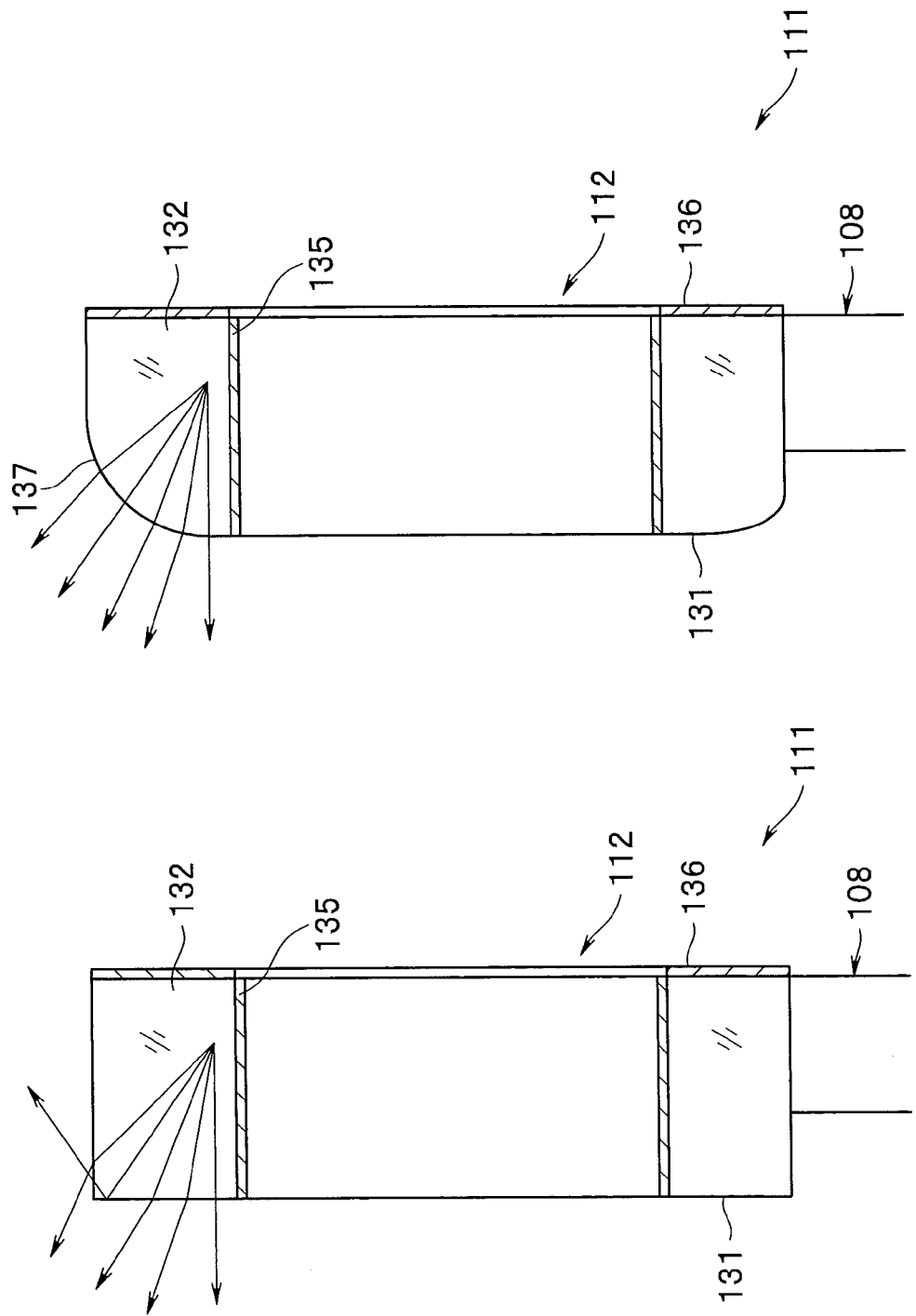

FIG.33
(A)
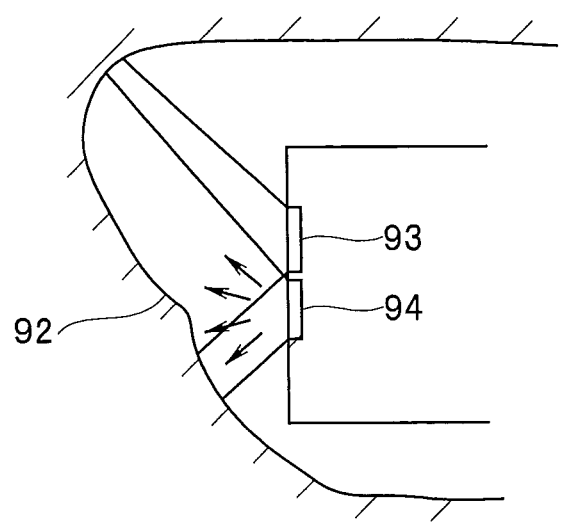
(B)
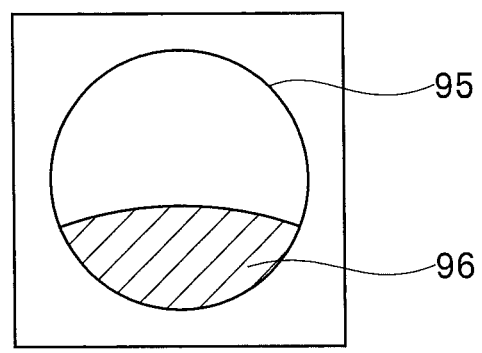

ENDOSCOPE AND ILLUMINATION APPARATUS FOR ENDOSCOPE

CROSS REFERENCE TO RELATED APPLICATION

This application is a continuation application of PCT/JP2012/058967 filed on Apr. 2, 2012 and claims benefit of Japanese Applications No. 2011-085315 filed in Japan on Apr. 7, 2011, No. 2011-246739 filed in Japan on Nov. 10, 2011, the entire contents of each of which are incorporated herein by their reference.

BACKGROUND OF THE INVENTION

1. Field of the Invention

The present invention relates to an endoscope including an illumination member that illuminates an object in an observation field of view and an illumination apparatus for an endoscope.

2. Description of the Related Art

In recent years, endoscopes with an observation window provided at a distal end portion of an insertion portion have widely been used in medical and other fields.

For clear observation of an object such as a diseased part in an observation field of view via an observation window, an illuminating window for making illuminating light exit to the observation field of view for illumination is provided at the periphery of the observation window.

For example, in FIG. 5 in Japanese Patent Application Laid-Open Publication No. 2008-155016 discloses an endoscope with an illuminating window disposed at each of two positions below an observation window.

SUMMARY OF THE INVENTION

An illumination apparatus for an endoscope according to an aspect of the present invention is an illumination apparatus for an endoscope, the illumination apparatus guiding externally-entering light to a transparent light-guiding body including an annular portion having an annular shape, the annular portion including an inner circumferential face and an outer circumferential face, and making the light exit from the annular portion as illuminating light, wherein the light-guiding body includes: a notch portion formed by cutting out a part of the annular portion so as to form a line extending perpendicularly from the outer circumferential face toward the inner circumference side of the annular portion from a line extending from a point on an outer circumference of a circle in a cross section of the annular portion; and an incident portion that allows the light to enter in a direction along the line extending from the point on the outer circumference, the direction being a direction perpendicular to a cutout surface of the notch portion provided in the annular portion.

An endoscope according to an aspect of the present invention includes, at a distal end portion of an insertion portion to be inserted into a body cavity, a forward-viewing observation window in which an objective lens for forward-viewing is provided, the forward-viewing observation window having a observation field of view for forward-viewing that is a forward side in an axis direction of the insertion portion, the illumination apparatus for an endoscope arranged in an illuminating window formed on an outer circumferential side of the forward-viewing observation window, the illumination apparatus guiding light entering a lower side of the observation field of view for forward viewing to make the illuminating light exit, and a light guide provided in the insertion portion of the endoscope, the light guide allowing light to enter the illumination apparatus for an endoscope.

BRIEF DESCRIPTION OF THE DRAWINGS

FIG. 21C is a diagram illustrating a manner in which illuminating light exits in each of cases where no curved surfaces are formed on the exit surface side and curved surfaces are formed on the exit surface side;

FIG. 33 is a diagram of a case where a close observation is performed in a conventional example.

DETAILED DESCRIPTION OF THE PREFERRED EMBODIMENTS

Embodiments of the present invention will be described below with reference to the drawings.
(First Embodiment)

Figure 1:
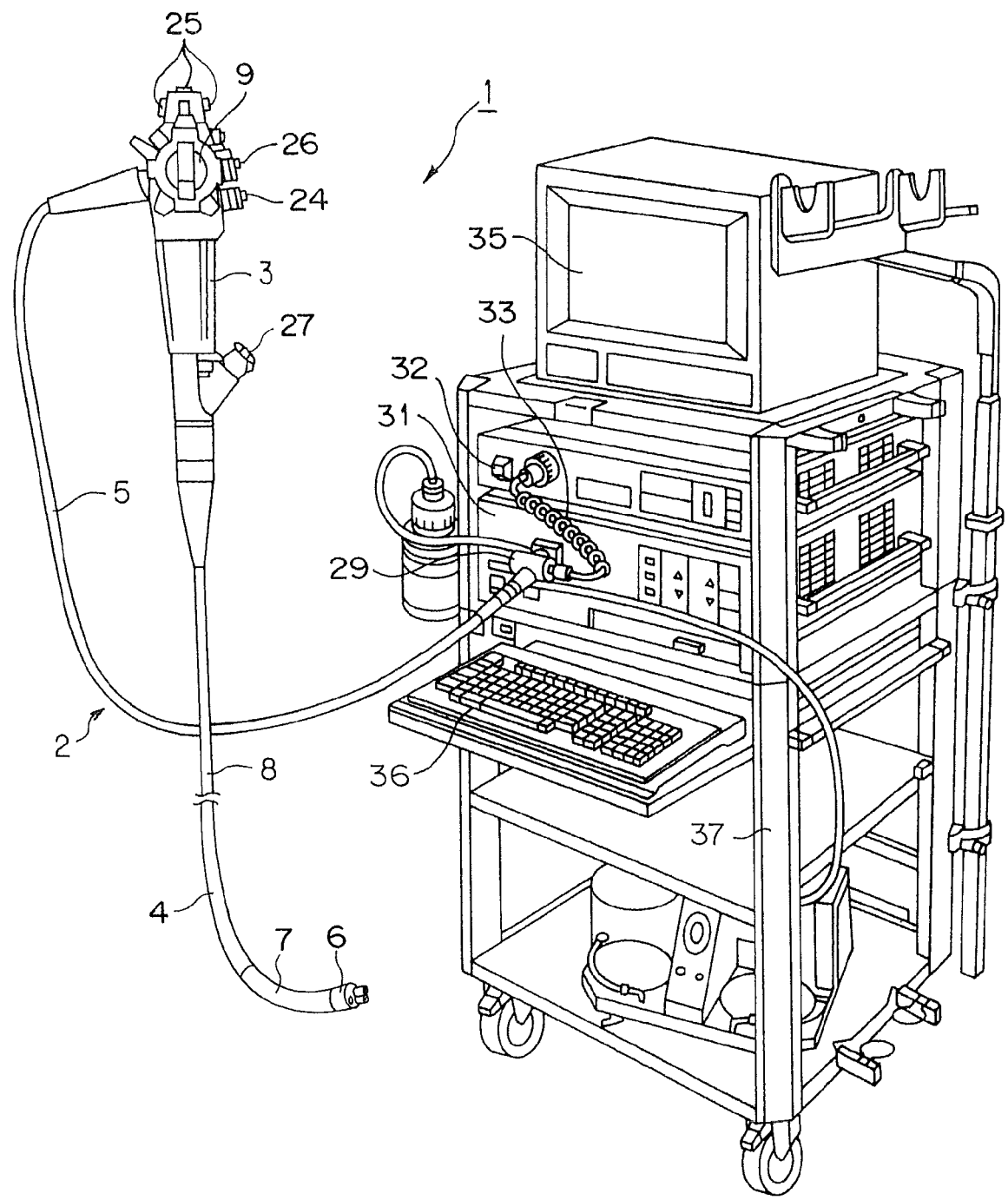
FIG. 1 is a perspective diagram illustrating an overall configuration of an endoscope apparatus including a first embodiment of the present invention.

As illustrated in FIG. 1, an endoscope apparatus 1 according to a first embodiment of the present invention includes an endoscope 2 that performs endoscopy. The endoscope 2 includes an operation portion 3 to be grasped by a surgeon to operate, an elongated insertion portion 4 formed at a front end of the operation portion 3, which is to be inserted into, e.g., a body cavity, and a universal cord 5 including a proximal end extending out from a side portion of the operation portion 3.

Furthermore, the insertion portion 4 includes a rigid distal end portion 6 provided at a distal end thereof, a bendable bending portion 7 provided at a rear end of the distal end portion 6, and a flexible tube portion 8 provided at a rear end of the bending portion 7, the flexible tube portion 8 having a long length and flexibility, and the bending portion 7 can be subjected to a bending operation by a bending operation lever 9 provided in the operation portion 3.

Figure 2:
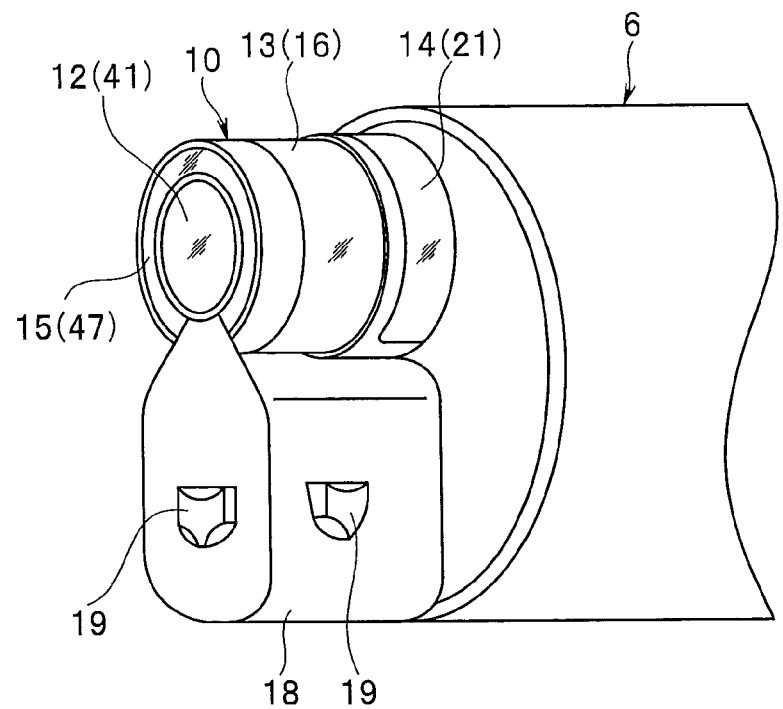
FIG. 2 is a perspective diagram illustrating a configuration of a distal end portion.

Furthermore, as illustrated in FIG. 2, at the distal end portion 6 of the insertion portion 4, a cylindrical distal end portion 10 is formed. The cylindrical distal end portion 10 projects from a decentered position in the vicinity of an upper central portion of a distal end face of the distal end portion 6 so as to form a cylindrical shape.

An objective lens system 11 (see FIG. 4) for both forward-viewing and side-viewing for performing an optical observation is attached to the distal end side of the cylindrical distal end portion 10, and a forward-viewing observation window 12 and a side-viewing observation window 13 are formed as observation windows for the objective lens system 11.

In the vicinity of a proximal end of the cylindrical distal end portion 10, a side-viewing illuminating window 14 that performs side-viewing illumination is formed. Also, on the outer circumferential side of the forward-viewing observation window 12, a forward-viewing illuminating window 15 having a C-ring shape excluding an outer circumferential part corresponding to the lower side of the forward-viewing observation window 12 (or an observation field of view for forward-viewing) is formed.

The side-viewing observation window 13 is formed so as to have a C-ring shape (substantially-annular shape) in order to make a nearly entire circumference of a side face (excluding on the lower end side) along a circumferential direction of the side face be included in an observation field of view for observation of a broad lateral range excluding the lower side. Note that the side-viewing illuminating window 14 also includes a C-ring-shaped side-viewing illumination member 21.

The side-viewing observation window 13 includes a mirror lens 16 as an objective lens for side-viewing, the mirror lens 16 including a reflective surface for capturing light from an object, which enters from an arbitrary side facing the substantially-annular shape (excluding the lower side) within an observation field of view for side-viewing (also referred simply as field of view for side-viewing) to obtain an image of the field of view for side-viewing.

On the other hand, a distal end lens 41 is attached to the forward-viewing observation window 12 as an objective lens for forward-viewing for obtaining an image of an object on the forward side of the forward-viewing observation window 12, that is, forward of the insertion portion 4 in an axis direction.

Also, at a part of the distal end face of the distal end portion 6 around the cylindrical distal end portion 10, a channel distal end opening portion 17 (see FIG. 3) is provided. The channel distal end opening portion 17 serves as an opening from which a treatment instrument inserted in a channel is made to project.

Furthermore, in the present embodiment, a cylindrical distal end portion support member (hereinafter, support member) 18 that supports the cylindrical distal end portion 10, the support member 18 being adjacent to the lower side of the cylindrical distal end portion 10, is provided so as to project from the distal end face of the distal end portion 6. The support member 18 reinforces a strength of the cylindrical distal end portion 10. Also, the support member 18 includes a light-blocking member having an optical blocking function.

Although in the present embodiment, the cylindrical distal end portion 10 and the support member 18 each include a same member, and the respective proximal ends thereof are provided integrally with the distal end face of the distal end portion 6 to form a distal end portion body portion (hereinafter, body portion) 51 (see FIG. 4), a structure in which the cylindrical distal end portion 10 and the support member 18 are fixed to the distal end portion 6 via bonding or otherwise may be provided.

In the support member 18, a nozzle portion 19 for a forward-viewing observation window, and a nozzle portion 20 for a side-viewing observation window for cleaning the forward-viewing observation window 12 and the side-viewing observation window 13 of the objective lens system 11 described above, respectively, are provided.

More specifically, at a distal end face of the support member 18, the nozzle portion 19 for a forward-viewing observation window, which opens toward the forward-viewing observation window 12, is provided.

Figure 3:
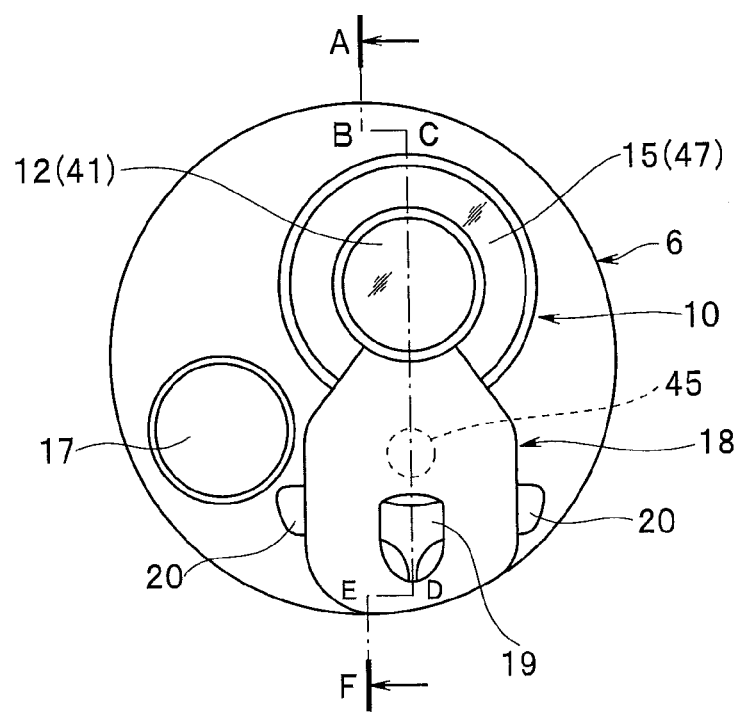
FIG. 3 is a front view of a distal end portion.

Also, at a side face of the support member 18, the nozzle portion 20 for a side-viewing observation window, which opens toward the side-viewing observation window 13, is provided, and the support member 18 blocks the nozzle portion 19 for a forward-viewing observation window and the nozzle portion 20 for a side-viewing observation window so as not to appear in an image of the field of view for side-viewing. Note that, as illustrated in FIG. 3, the nozzle portion 20 for a side-viewing observation window is provided at each of two positions.

In the operation portion 3 illustrated in FIG. 1, an air/liquid feeding operation button 24 is provided so that an air and a liquid for cleaning are selectively injected from each of the nozzle portion 19 for a forward-viewing observation window and the nozzle portions 20 for a side-viewing observation window, and switching between air feeding and liquid feeding can be made by operating the air/liquid feeding operation button 24.

Note that although the example illustrated in FIG. 1 indicates an example in which one air/liquid feeding operation button 24 is provided, two air/liquid feeding operation buttons 24 may be provided.

Also, in the operation portion 3, a suction operation button 26 for sucking and collecting, e.g., mucus inside a body cavity via the channel distal end opening portion 17 is disposed. Note that the channel includes, e.g., a tube disposed inside the insertion portion 4 and is in communication with a treatment instrument insertion port 27 provided in the vicinity of a front end of the operation portion 3.

When a surgeon intends to perform a treatment using a treatment instrument, the surgeon inserts the treatment instrument from the treatment instrument insertion port 27 and makes the distal end side of the treatment instrument project from the channel distal end opening portion 17, whereby a treatment for therapy using the treatment instrument can be performed.

Also, a connector 29 is provided at a terminal of the universal cord 5, and the connector 29 is connected to a light source apparatus 31 for an endoscope. A pipe sleeve (not illustrated), which serves as a connection end portion of a fluid conduit projecting from a distal end of the connector 29, and a light guide pipe sleeve (not illustrated), which serves as an end portion of illuminating light supply, are detachably connected to the light source apparatus 31, and an end of a connection cable 33 is connected to an electric contact portion provided at a side face.

Also, a connector at the other end of the connection cable 33 is electrically connected to a video processor 32, which serves as a signal processing apparatus that performs signal processing for an image pickup device 34 (see FIG. 4) included in an image pickup unit 52 installed in the distal end portion 6 of the endoscope 2.

The video processor 32 supplies a drive signal for driving the image pickup device 34 installed in the distal end portion 6 of the endoscope 2 and performs signal processing on an image pickup signal (image signal) outputted from the image pickup device 34 as a result of the supply of the drive signal to generate a video signal.

The video signal generated by the video processor 32 is outputted onto a monitor 35, which serves as a display apparatus, and on a display screen of the monitor 35, an image picked up by the image pickup device 34 is displayed as an endoscopic image. Peripheral apparatuses such as the light source apparatus 31, the video processor 32 and the monitor 35 are arranged on a rack 37 together with a keyboard 36 via which, e.g., patient information is inputted.

Figure 4:
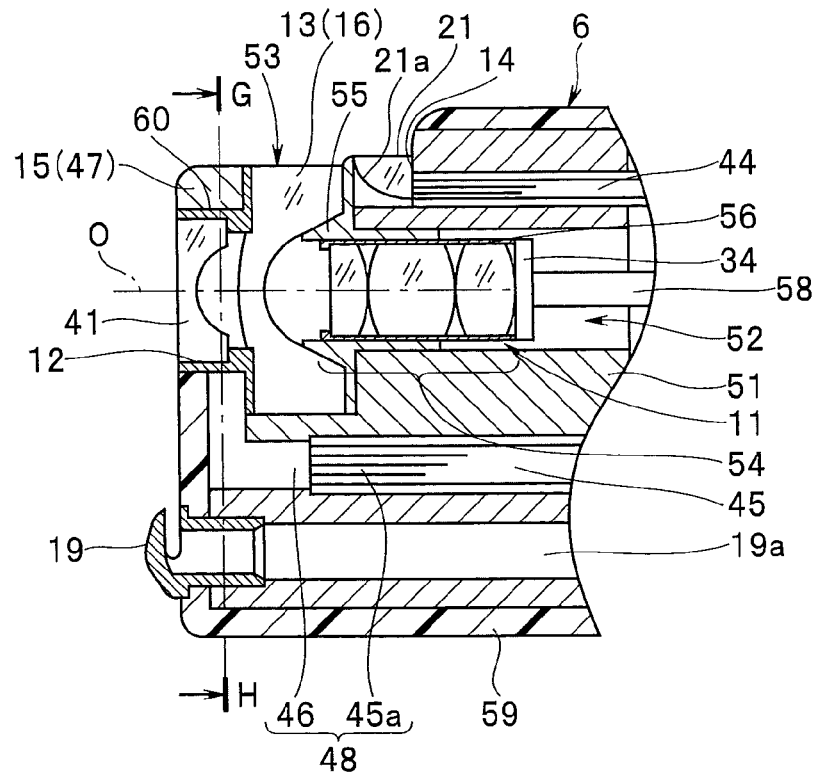
FIG. 4 is a vertical cross-sectional view taken along line A-B-C-D-E-F in FIG. 3.

Illuminating light generated in the light source apparatus 31 is guided (conveyed) by one light guide inserted inside the universal cord 5 and the operation portion 3, and further guided (conveyed) to the distal end face side by light guides 44 and 45 resulting from the light guide being branched into a plurality of light guides inside the insertion portion 4 (see FIG. 4).

A distal end portion of the light guide 44 extending inside the insertion portion 4 is arranged on the inner side of the side-viewing illuminating window 14 of the cylindrical distal end portion 10, thereby serving as a light exit member from which light guided from the light source apparatus 31 exits. The light exiting forward in the axis direction of the distal end portion 6 from a distal end face of the light guide 44 is reflected substantially perpendicularly by a recessed reflective surface 21a provided at the side-viewing illumination member 21 and exits laterally, and illuminating light exits toward the observation field of view for side-viewing via a transparent member 21b covering the reflective surface 21a.

Also, the reflective surface 21a provided in the side-viewing illumination member 21 is formed so as to have a C-ring shape excluding the support member 18 on the lower side, and makes illuminating light exit toward the nearly entire circumference of the field of view for side-viewing excluding the lower side.

Also, a distal end portion of the light guide 45 extending inside the insertion portion 4 (as indicated by a dotted line in FIG. 3) is arranged inside a light guide insertion hole provided inside the support member 18.

The distal end portion of the light guide 45 forms a light exit member 45a that makes light guided from the light source apparatus 31 exit. Light exiting forward of the distal end portion 6 in the axis direction from a distal end face of the light exit member 45a (distal end face of the light guide 45) fall on incident surfaces 47a and 47b (see FIGS. 6 and 8A) of a C-ring-shaped light-guiding plate 47 formed at the outer circumference of the forward-viewing observation window 12 via a light-guiding member 46 formed in an L-shape.

In the present embodiment, the distal end portion of the light guide 45, which serves as the light exit member 45a, and the light-guiding member 46 form a light exit portion 48 that makes light exit so that the light falls on the incident surfaces 47a and 47b of the light-guiding plate 47.

Note that in a modification (FIG. 10) described later, light-emitting diodes (abbreviated as LEDs) 61a and 61b, which serve as light-emitting devices, form a light exit portion that makes light exit so that the light generated by the LEDs 61a and 61b directly fall on the incident surfaces 47a and 47b of the light-guiding plate 47 without using the light-guiding member 46.

Figure 5:
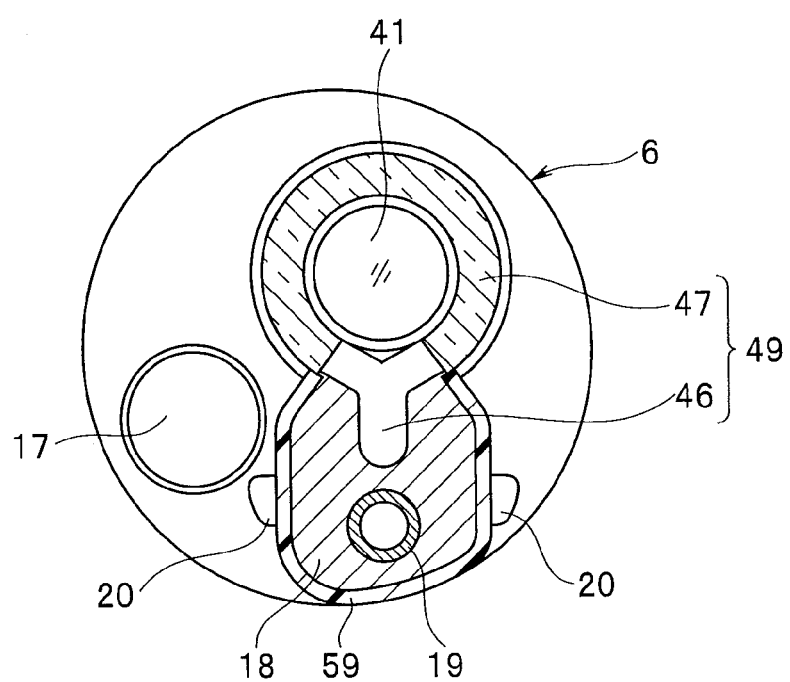
FIG. 5 is a horizontal cross-sectional view taken along line G-H in FIG. 4.

FIG. 5 illustrates an illumination member 49 part for forward-viewing illumination including the light-guiding member 46 for forward-viewing illumination and the C-ringshaped light-guiding plate 47 in a cross-section along line G-H in FIG. 4. Also, FIG. 6A illustrates a schematic shape of the illumination member 49.

Figure 6:
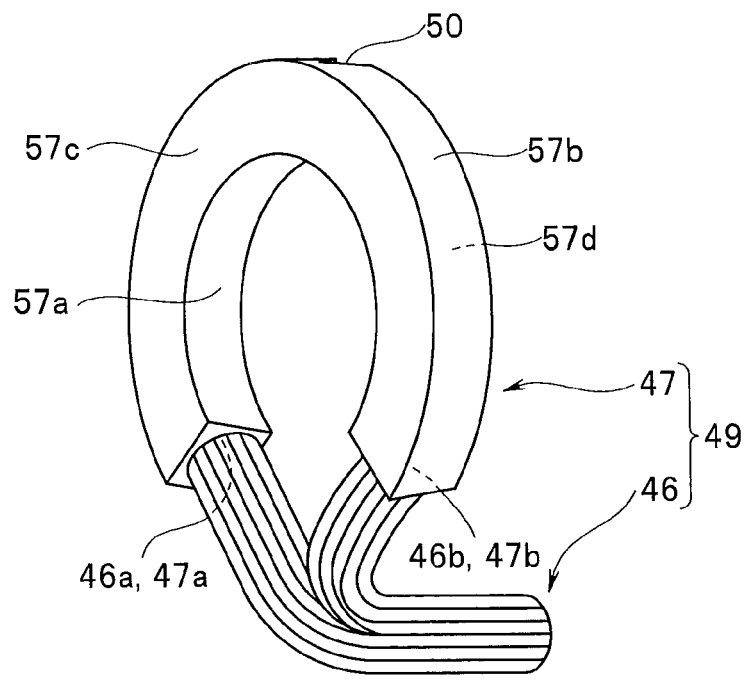
FIG. 6 is a perspective diagram illustrating a schematic shape of an illumination member.

As illustrated in the vertical cross-sectional view in FIG. 4, the light-guiding member 46 has an L-shape in the axis direction of the distal end portion 6; however, as illustrated in the horizontal cross-sectional view in FIG. 5, the distal end side thereof is formed in a shape branched so as to have a V-shape (substantially Y-shape where the proximal end side is included). Note that as illustrated in FIG. 6, the light-guiding member 46 may include, for example, a rigid fiber bundle.

Then, a proximal end face of the light-guiding member 46, for example, closely adheres to or closely contacts (at least faces) the distal end face of the light guide 45, and the light-guiding member 46 guides light exiting from the distal end face to the distal end side flexed in an L-shape, and using the distal end faces resulting from the branching in a V-shape on the distal end side as exit surfaces 46a and 46b, makes the guided light exit. The exit surfaces 46a and 46b closely adhere to or closely contact the incident surfaces 47a and 47b of the C-ring-shaped light-guiding plate 47, and light exiting from the exit surfaces 46a and 46b fall on the incident surfaces 47a and 47b, respectively.

The light falling on the incident surfaces 47a and 47b is guided by the C-ring-shaped light-guiding plate 47 as described later, and is made to exit forward from a front face of the C-ring-shaped light-guiding plate 47 to provide forward-viewing illuminating light that illuminates an object (such as a site to be observed) in the field of view for forward-viewing.

Also, in the present embodiment, at a position in the vicinity of an upper portion of the C-ring-shaped light-guiding plate 47, a wedge-shaped reflective surface 50 (see FIGS. 6, 8A and 8B) formed by cutting out a part of the light-guiding plate 47 from a back face toward the front face into a wedge shape is provided so that guided light exits forward (toward the front side).

Also, as illustrated in FIG. 4, the image pickup unit 52 is incorporated along a center axis of the cylindrical distal end portion 10. In the image pickup unit 52, a front lens portion 53 and a rear lens portion 54 included in the objective lens system 11 are attached to lens barrels 55 and 56, respectively, so that the center axis of the cylindrical distal end portion 10 is an optical axis O.

The front lens portion 53 includes a distal end lens 41 and a mirror lens 16 attached to a front lens barrel 60, each having a rotation symmetrical shape, and the lens barrel 55 is attached to a rear face of the mirror lens 16.

Furthermore, the rear lens portion 54 includes a plurality of lenses attached to the lens barrel 56, and the image pickup device 34 is also attached to the lens barrel 56. Then, both of the lens barrels 55 and 56, which fit together in such a manner that the lens barrels 55 and 56 can move in the optical axis O direction, are fixed inside the body portion 51 after both of the lens barrels 55 and 56 are relatively moved to enter a state in which the respective focuses of the lens barrels 55 and 56 are adjusted.

An outer diameter of the front lens barrel 60 (excluding a stepped portion at the rear end) is almost equal to an inner diameter of the C-ring-shaped light-guiding plate 47, and fixed in a state in which the front lens barrel 60 fits on an inner circumferential face of the light-guiding plate 47.

The image pickup device 34 is connected to a signal cable 58 at a back face thereof.

Note that an outer circumferential face of the body portion 51 of the distal end portion 6 and a front face of the support member 18 are covered by a cover member 59. Also, the nozzle portion 19 for a forward-viewing observation window is attached to a distal end opening of a hollow portion 19a provided in the support member 18.

Note that as illustrated in FIG. 6, the C-ring-shaped light-guiding plate 47 is provided with reflective surfaces 57a and 57b, which reflect light, at the inner circumferential face and an outer circumferential face thereof, a scattering reflective surface 57d, which serves as a reflective surface that reflects light in a scattered manner, at a back face thereof, and a transmissive surface 57c, which transmits light to make the light exit to the observation field of view for forward-viewing as illuminating light, at a front face thereof, respectively.

Figure 7:
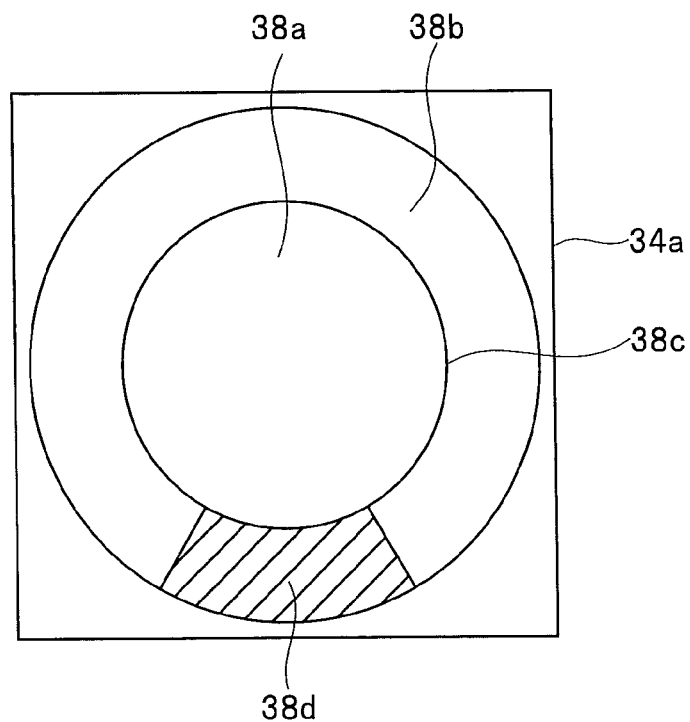
FIG. 7 is a diagram illustrating a circular region and an annular region in which an object image for forward-viewing and an object image for side-viewing are formed on an image pickup surface of an image pickup device, respectively.

As illustrated in FIG. 7, an object image for forward-viewing and an object image for side-viewing are formed on a circular region 38a and an annular region (C-ring region) 38b of an image pickup surface 34a of the image pickup device 34, respectively, via the objective lens system 11.

In the circular region 38a at a center of a rectangular region forming the image pickup surface 34a, an object image for forward-viewing passed through the distal end lens 41 in the forward-viewing observation window 12 is formed, and in the annular region 38b outside the circular region 38a, an object image for side-viewing passed through the mirror lens 16 in the side-viewing observation window 13 is formed so as to be concentric to the object image for forward-viewing. Note that reference numeral 38c denotes a circular part that serves as a boundary between the object image for forward-viewing and the object image for side-viewing.

However, in the present embodiment, light from the object side, which enters the side-viewing observation window 13 side, is mechanically blocked by the support member 18, and thus, a lower-side region 38d inside the annular region 38b becomes a non-image-pickup region for which no image is picked up by the image pickup device 34.

The endoscope 2 according to the present embodiment, which is configured as described above, includes, at the distal end portion 6 of the insertion portion 4, the forward-viewing observation window 12 provided with the distal end lens 41, which serves as an objective lens for forward-viewing for the observation field of view for forward-viewing on the forward side of the insertion portion 4 in the axis direction, the C-ring-shaped light-guiding plate 47 disposed on the outer circumferential side of the forward-viewing observation window 12, in which the scattering reflective surface 57d that serves as a reflective surface that reflects light and the transmissive surface 57c that transmits light and makes the light exit to the observation field of view for forward-viewing as illuminating light are formed at the back face and the front face, respectively, and an outer circumferential part corresponding to the lower side of the observation field of view for forward-viewing is cut out, and the light-guiding member 46 that forms a light exit portion that makes light exit so as to fall on the incident surfaces 47a and 47b that are end faces resulting from the light-guiding plate 47 being cut so as to have a C-ring shape, and at the position on the upper side of the light-guiding plate 47, the wedge-shaped reflective surface 50 formed by a part of a back face of the light-guiding plate 47 being cut out toward the front face of the light-guiding plate 47 so as to form a wedge shape in order to make guided light exit to the front side of the light-guiding plate 47.

Next, e.g., a configuration of a portion in the periphery of the illumination member 49 in the present embodiment will be described mainly with reference to FIGS. 6 and 8A-8C.

As illustrated in these Figures, the light-guiding plate 47 includes an inner circumferential face having a predetermined inner diameter d1 and an outer circumferential face having a predetermined outer diameter d2, and has a C-ring shape that is a circular ring with its lower side cut out.

Figure 8A:
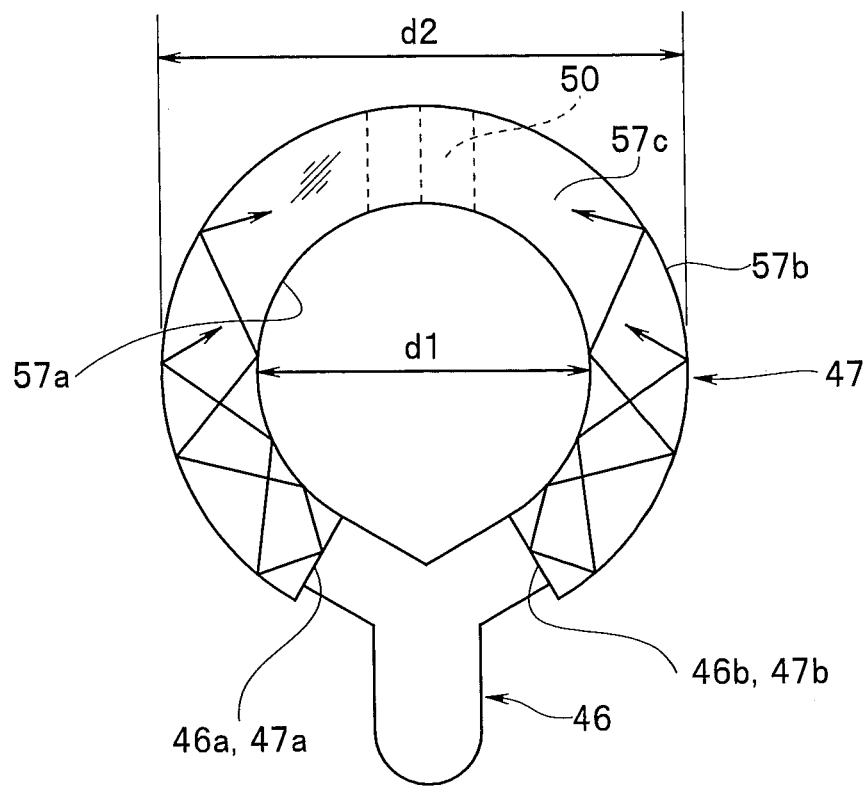
FIG. 8A is a front view illustrating an illumination member.

Also, as illustrated in FIGS. 6 and 8A, the inner circumferential face and the outer circumferential face of the light-guiding plate 47 are provided with the reflective surfaces 57a and 57b, respectively, so that light entering from the light-guiding member 46 via the incident surfaces 47a and 47b on the lower end side can efficiently be made to exit from the front face. A metal film for reflection, which is of, e.g., aluminum or silver and has a high reflection function, is provided at the inner circumferential face and the outer circumferential face of the light-guiding plate 47, whereby the reflective surfaces 57a and 57b are formed, respectively.

Figure 8B:
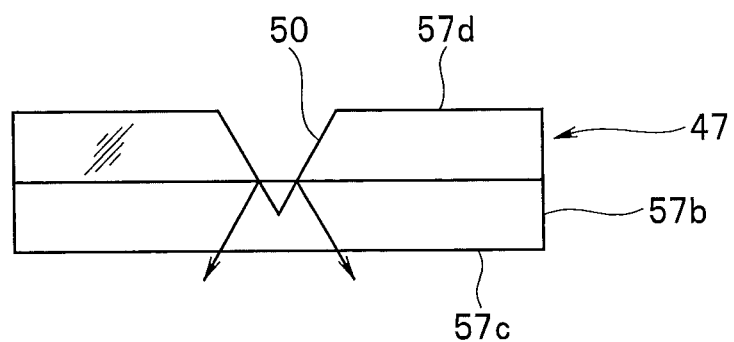
FIG. 8B is a plan view from the top of FIG. 8A.
Figure 8C:
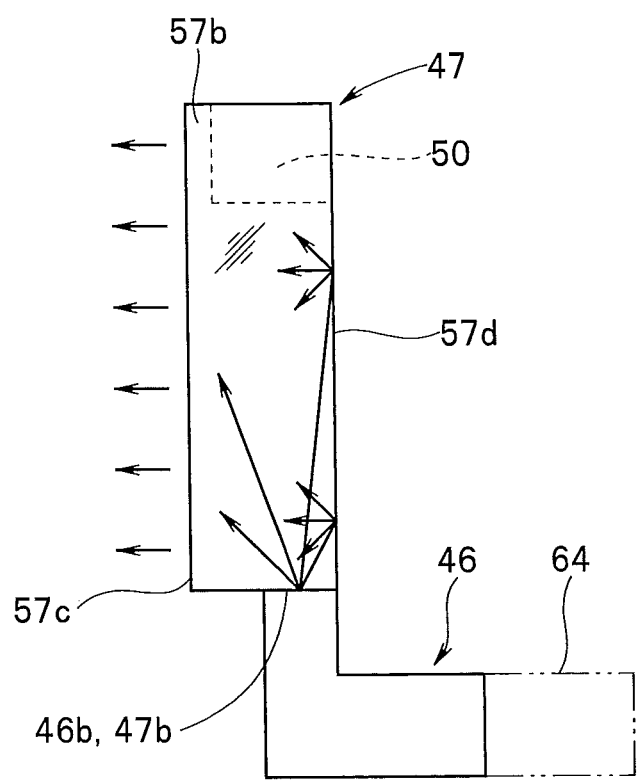
FIG. 8C is a side view from the right side of FIG. 8A.

Also, at the back face of the light-guiding plate 47, a small-projection and recess portion is provided, and at a surface of the small-projection and recess portion, a metal film for reflection, which is of, e.g., aluminum or silver and has a high reflection function, is provided to form the scattering reflective surface 57d that reflects incident light in a scattered manner as illustrated in FIG. 8C. Note that the front face of the light-guiding plate 47 serves as the transmissive surface (exit surface) 57c that makes light transmitted by the light-guiding plate 47 exit as forward-viewing illuminating light.

Also, in the present embodiment, a structure in which a part in the vicinity of an upper position in the light-guiding plate 47 is cut out into a wedge shape and a metal film for reflection is provided on an end face of the cutout part having the wedge shape to form the reflective surface 50 to make light guided by the reflective surface 50 efficiently exit forward or to the front side is employed. The wedge-shaped cutout has a thickness, for example, equal to or exceeding ½, for example, around ⅔-⅚, of a thickness between the front face and the rear face of the light-guiding plate 47.

An operation of the present embodiment with the configuration described above will be described. Illuminating light generated by the light source apparatus 31 falls on an incident end face of the light guide inserted inside the universal cord 5 in the endoscope 2 and guided by the light guide. The light guide is branched into the light guides 44 and 45 inside the insertion portion 4.

The light guide 44 makes the guided light exit from the distal end face thereof. The reflective surface 21a is provided so as to face the distal end face. The reflective surface 21a reflects light exiting from the distal end face of the light guide 44 to make illuminating light exit laterally from the side-viewing illuminating window 14, thereby illuminating the object side in the field of view for side-viewing. Note that in reality, the light guide 44 is arranged at each of a plurality of positions in a circumferential direction.

Also, the light guide 45 makes the guided light exits from the distal end face thereof, and makes the exiting light fall on the proximal end face of the light-guiding member 46, which faces the distal end face of the light guide 45, e.g., in close contact with the proximal end face. The light-guiding member 46 guides the entering light to the distal end side, which is flexed in an L-shape, and make the guided light exit from the exit surfaces 46a and 46b, which are branched so as to form a V-shape.

The exit surfaces 46a and 46b closely contact or abut to the incident surfaces 47a and 47b of the C-ring-shaped light-guiding plate 47, whereby light exiting from the exit surfaces 46a and 46b efficiently fall on the incident surfaces 47a and 47b, respectively.

As illustrated in FIG. 8A, at the inner circumferential face and the outer circumferential face of the light-guiding plate 47, the respective reflective surfaces 57a and 57b are formed, and thus, as illustrated in FIG. 8A, light entering the inside of the light-guiding plate 47 is guided while being reflected by the reflective surfaces 57a and 57b.

Furthermore, light guided to the back side is scattered as described below and light guided to the front side passes through the transmissive surface 57c, which is the front face, and exits forward as forward-viewing illuminating light.

Also, as illustrated in FIG. 8C, the scattering reflective surface 57d is provided at the back face of the light-guiding plate 47, and light falling on the back face is scattered and exits forward from the front face of the light-guiding plate 47 or the transmissive surface 57c at the front face after being reflected by the reflective surfaces 57a and 57b.

Also, in the present embodiment, at the position in the upper portion of the light-guiding plate 47, the wedge-shaped reflective surface 50 is provided, and thus, for example, if light guided into the light-guiding plate 47 runs in an upward direction on the surface of the sheet of FIG. 8C, as illustrated in FIG. 8B, the light is reflected by the reflective surface 50 to make the light exit from the front face.

On the other hand, if the wedge-shaped reflective surface 50 is not provided, for example, light entering from the incident surface 47a is guided to the other incident surface 47b side as a result of being reflected by the reflective surfaces 57a and 57b, increasing the ratio of the light that cannot be used for illuminating light made to exit from the front face. In order to supplement this, it is necessary to increase the size of the light-guiding plate or increase the size of the light guide to increase light guided by, e.g., the light-guiding member.

However, in the present embodiment, light entering from one incident surface and guided to the other incident surface is reflected by the wedge-shaped reflective surface 50 at a partway point so as to exit from the front face, enhancing the ratio of the light that can be used for illuminating light.

Then, light exiting from the front face of the light-guiding plate 47 illuminates the object side in the observation field of view for forward-viewing. In this case, the ratio of the light that can be used for illuminating light can be enhanced, enabling a necessary amount of illuminating light to be secured without an increase in size of the light-guiding plate 47. Accordingly, an increase in size of the distal end portion 6 can be prevented, enabling downsizing.

Figure 9A:
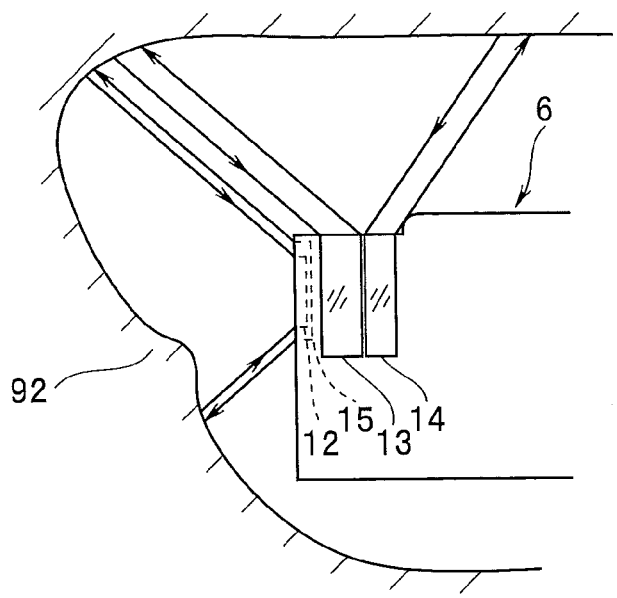
FIG. 9A is a diagram illustrating a manner in which a site to be observed is closely observed.
Figure 9B:
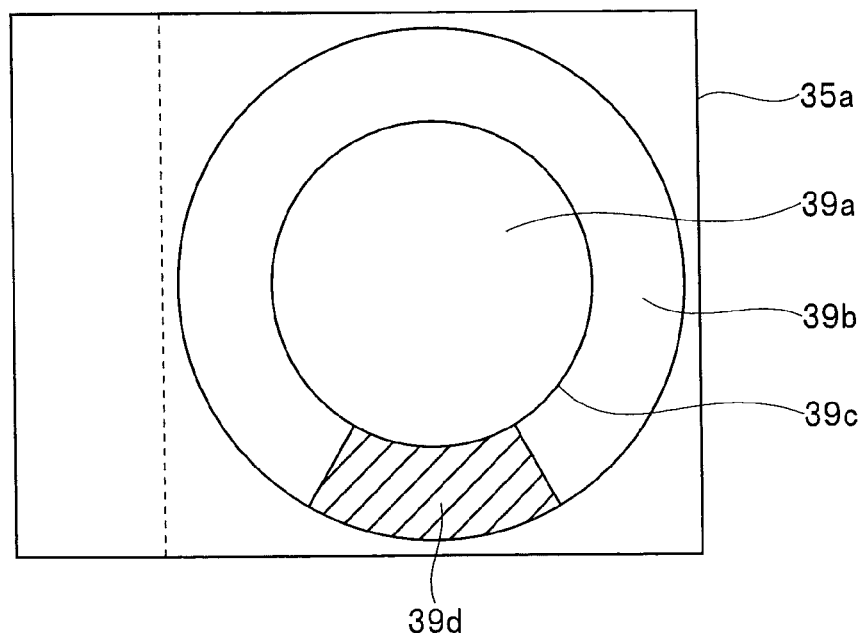
FIG. 9B is a diagram illustrating a display screen of a monitor in the case of FIG. 9A.

FIG. 9A illustrates a manner in which a site to be observed 92 such as a diseased part in a body cavity is closely observed using the endoscope 2 according to the present embodiment, and FIG. 9B illustrates a display screen 35a of the monitor 35 in such case. A circular region 39a and an annular region 39b in FIG. 9B indicate image display regions corresponding to the circular region 38a and the annular region 38b illustrated in FIG. 7 in which an object image for forward-viewing and an object image for side-viewing are formed, respectively.

Furthermore, reference numeral 39c denotes a circular part that is a boundary between an image display region for forward-viewing and an image display region for side-viewing. Also, a region 39d, which is indicated by shading on the lower side of the annular region 39b, is a non-display region corresponding to the region 38d in FIG. 7, in which no image is displayed.

In the present embodiment, since the forward-viewing illuminating window 15 is formed in a C-ring shape so as to exclude a lower-side part from the outer circumference of the forward-viewing observation window 12, even when an observation is performed with the distal end face of the distal end portion 6 close to the site to be observed 92, illumination and observation can be performed with no halation occurring on the lower side.

Figure 18:
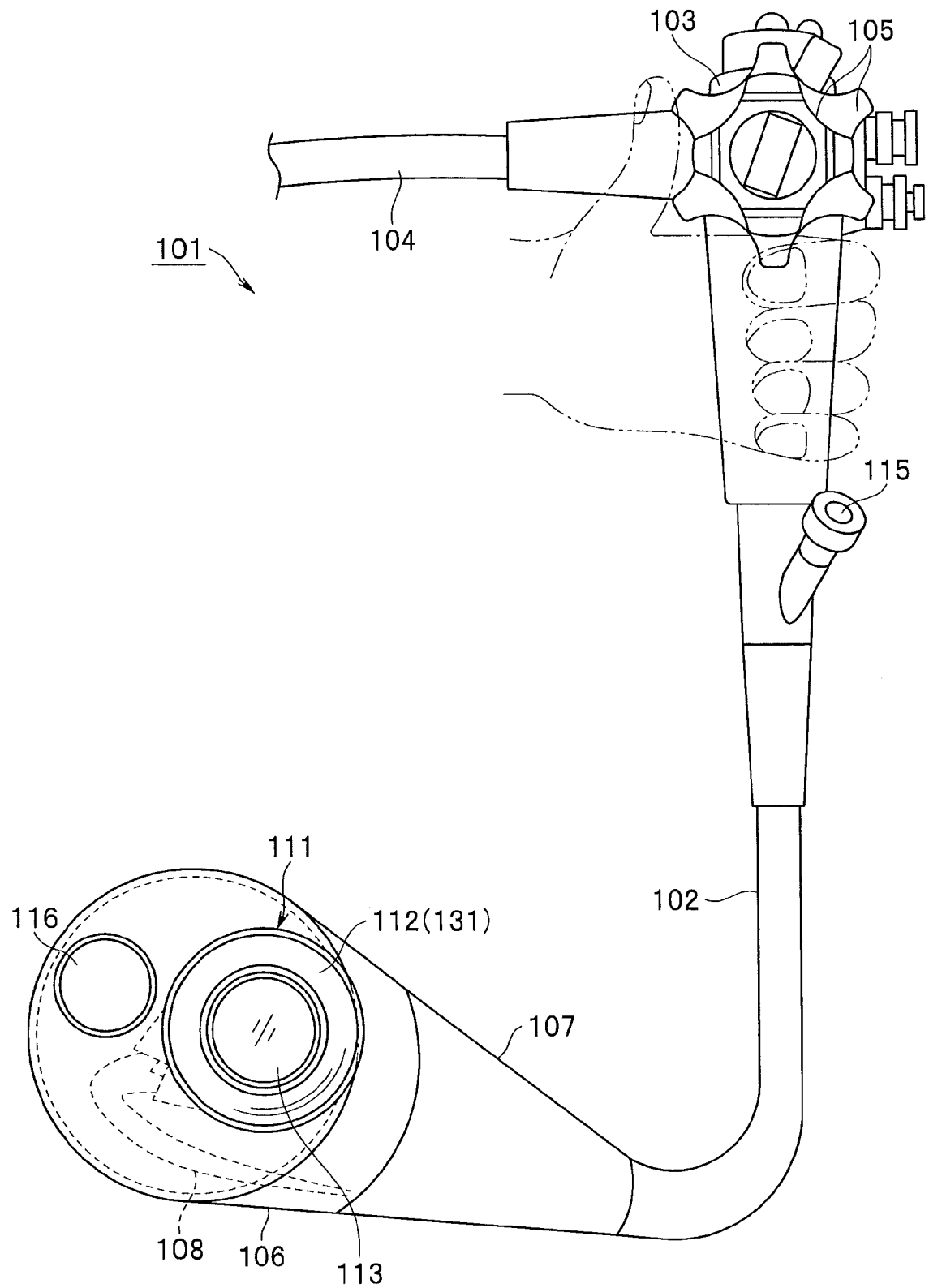
FIG. 18 is a perspective diagram illustrating an endoscope to which an illumination apparatus for an endoscope according to a fourth embodiment of the present invention is applied.

In other words, the present embodiment can effectively prevent halation from occurring as a result of increasing an intensity of illuminating light at a part facing the lower side relative to the upper side as in the conventional example in FIG. 18.

Furthermore, the present embodiment enables illumination with reduced illumination unevenness in the observation field of view for forward-viewing because the forward-viewing illuminating window 15 is formed so as to have a C-ring shape surrounding the outer circumference of the forward-viewing observation window 12 and excluding the lower-side part as described above. In other words, illumination of good quality can be performed. Thus, an observation image facilitating diagnosis can be provided for a surgeon.

Also, the present embodiment enables provision of a distal end portion 6 with a compact size when a C-ring-shaped side-viewing observation window 13 is formed behind and adjacent to a forward-viewing observation window 12 to form an image pickup unit 52 enabling forward-viewing and side-viewing.

More specifically, not a structure in which light enters from the back side of the C-ring-shaped light-guiding plate 47, but a structure in which light enters from the incident surfaces 47a and 47b on the lower side (of the forward-viewing observation window 12), which has been cut out to form a C-ring shape, into the C-ring-shaped light-guiding plate 47 is employed, and thus, as illustrated in FIG. 4, the side-viewing observation window 13 can be formed adjacent to the back face of the light-guiding plate 47, enabling the length of the distal end portion 6 to be short.

On the other hand, in the case of a structure in which light enters from the back side of the C-ring-shaped light-guiding plate 47, a space in which, e.g., a light-emitting device and a light-guiding member for entrance of light are arranged is required, resulting the length of the distal end portion 6 being long.

Furthermore, according to the present embodiment, the efficiency of use of light guided into the light-guiding plate 47 as illuminating light actually exiting to the observation field of view can be enhanced by the wedge-shaped reflective surface 50, enabling reduction in size of the illumination member 49 including the light-guiding member 46 and the light-guiding plate 47, and also enabling reduction in size of the distal end portion 6.

Furthermore, according to the present embodiment, both an observation image for forward-viewing and an observation image for side-viewing can simultaneously be obtained and displayed, enabling smooth endoscopy relative to a case of one observation image.

Note that although in the above-described first embodiment, the proximal end face of the light-guiding member 46 is fixed to the distal end face of the light guide 45 so as to closely contact or abut to the distal end face of the light guide 45, facilitating the assembly, the present invention is not limited to this case, and one resulting from the light-guiding plate 47 being molded integrally with the distal end face of the light guide 45 may be employed.

Furthermore, although the first embodiment employs a structure in which the light-guiding member 46 and the light-guiding plate 47 are assembled together as separate members, the present invention is not limited to this case, and one resulting from a light-guiding member 46 and a light-guiding plate 47 being integrally molded may be employed.

Figure 10:
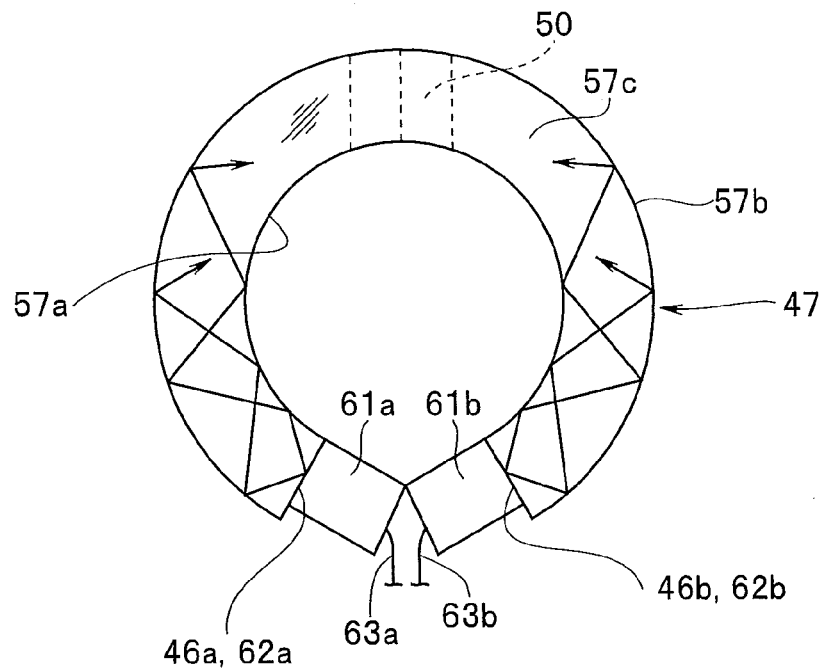
FIG. 10 is a diagram illustrating a light-guiding plate and LEDs included in a light exit portion in a modification.

Furthermore, although the above-described first embodiment employs a structure provided with the light-guiding member 46, as in the modification illustrated in FIG. 10, a structure in which light generated from, for example, exit surfaces 62a and 62b of LEDs 61a and 61b falls on respective incident surfaces 47a and 47b of a light-guiding plate 47 without using a light-guiding member 46 may be employed.

The LEDs 61a and 61b are connected to an LED power supply circuit provided in a light source apparatus 31 via respective drive lines 63a and 63b, and the LEDs 61a and 61b are put on by LED power supplied from the LED power supply circuit via the drive lines 63a and 63b.

In the configuration of the present modification, the LEDs 61a and 61b provides a light exit portion that makes light exit so as to fall on the incident surfaces 47a and 47b of the light-guiding plate 47.

Operations and effects of the present modification are substantially similar to those of the first embodiment. Note that in the case of the present modification, the other light guide 44 may be used as illustrated in FIG. 4 or a structure not using the light guide 44 may be employed by not using the light guide 44 but arranging an LED at the position of the distal end face of the light guide 44.

Furthermore, for another modification, as indicated by the alternate long and two short dashes line in FIG. 8C, light generated by an LED 64 may be made to enter a light-guiding member 46 without using a light guide 45 as a light exit member.

(Second Embodiment)

Figure 11:
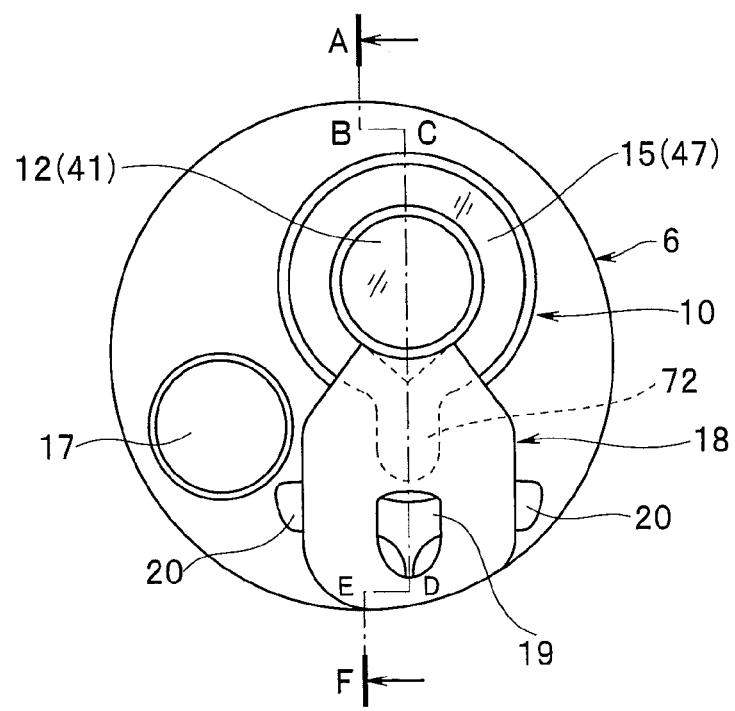
FIG. 11 is a front view of a distal end portion in a second embodiment of the present invention.
Figure 12:
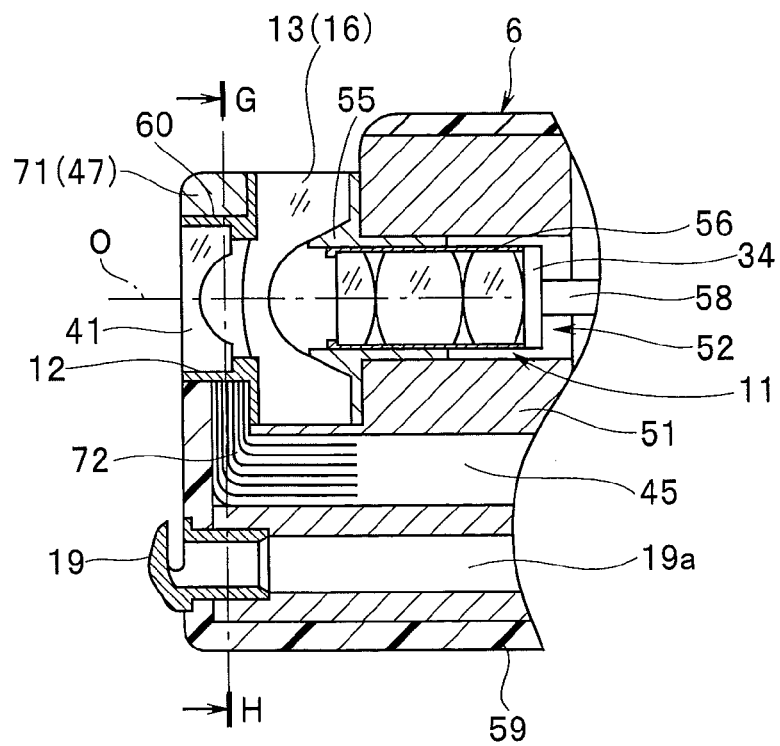
FIG. 12 is a vertical cross-sectional view taken along line A-B-C-D-E-F in FIG. 11.
Figure 13:
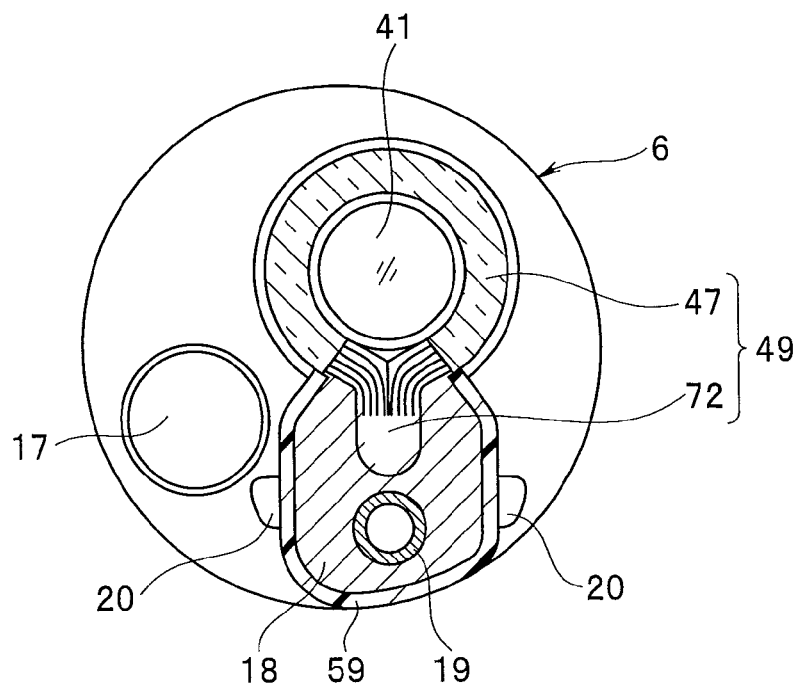
FIG. 13 is a horizontal cross-sectional view taken along line G-H in FIG. 12.

Next, a second embodiment of the present invention will be described. FIGS. 11 and 12 are a front view and a vertical cross-sectional view illustrating a structure of a distal end portion of an endoscope according to a second embodiment of the present invention. Also, FIG. 13 is a horizontal cross-sectional view of FIG. 12.

The present embodiment is different from the first embodiment only in terms of a part of a structure inside a distal end portion 6, and thus, only the part different from the first embodiment will be described.

Although in the first embodiment, the side-viewing illuminating window 14 that performs side-viewing illumination using light guided by the light guide 44 is formed behind and adjacent to the side-viewing observation window 13, in the present embodiment, the side-viewing illuminating window 14 is not provided, but a forward-viewing/side-viewing illuminating window 71 that performs both forward-viewing illumination and side-viewing illumination is provided.

Then, in the present embodiment, the light guide 45 according to the first embodiment is used and the forward-viewing/side-viewing illuminating window 71 is formed on a distal end of the light guide 45.

Although the light guide 45 according to the first embodiment is arranged inside the support member 18 so that the distal end face of the light guide 45 closely contact or abuts to the proximal end face of the light-guiding member 46, in the present embodiment, the distal end side of the light guide 45 is flexed in an L-shape and the flexed distal end side is branched to form a V-shape and the distal end faces resulting from the branching are arranged to closely contact or abut to incident surfaces 47a and 47b of a C-ring-shaped light-guiding plate 47, in order to double as a function of the light-guiding member 46 in the first embodiment.

However, in the present embodiment, an outer diameter of the light guide 45 is made to be larger than that of the first embodiment so that an amount of illuminating light necessary for forward-viewing and side-viewing can be guided.

Reference numeral 72 denotes a light-guiding portion of the light guide 45 in the present embodiment, which has a function of a light-guiding member 46.

Distal end faces in a branched V shape of the light-guiding portion 72 serve as exit surfaces 72a and 72b that make light exit so as to fall on incident surfaces 47a and 47b of the light-guiding plate 47. In FIG. 11, the light-guiding portion 72 is indicated by dotted lines. Also, FIG. 13 illustrates a structure in which the light-guiding member 46 in FIG. 5 is replaced with the light-guiding portion 72.

Also, FIG. 12 illustrates a structure in which the light-guiding member 46 in FIG. 4 is replaced with the light-guiding portion 72 and a light guide 44 and a side-viewing illumination member 21 for side-viewing illumination are not provided. Since no space for arranging a side-viewing illuminating window 14 is provided, the distal end portion 6 illustrated in FIG. 12 has a size having a small length relative to the distal end portion 6 in FIG. 4. Note that reference numerals 53 and 54 are omitted in FIG. 12.

The present embodiment employs a structure in which forward-viewing illumination and side-viewing illumination are performed from the forward-viewing/side-viewing illuminating window 71, by slightly changing the configuration of the light-guiding plate 47 in the first embodiment. Note that a front face of the forward-viewing/side-viewing illuminating window 71 at which (a front face) of the light-guiding plate 47 is exposed serves as a forward-viewing illuminating window that makes forward-viewing illuminating light exit, and a side face of the forward-viewing/side-viewing illuminating window 71 at which an outer circumferential face of the light-guiding plate 47 is exposed serves as a side-viewing illuminating window that makes side-viewing illuminating light exit.

Figure 14A:
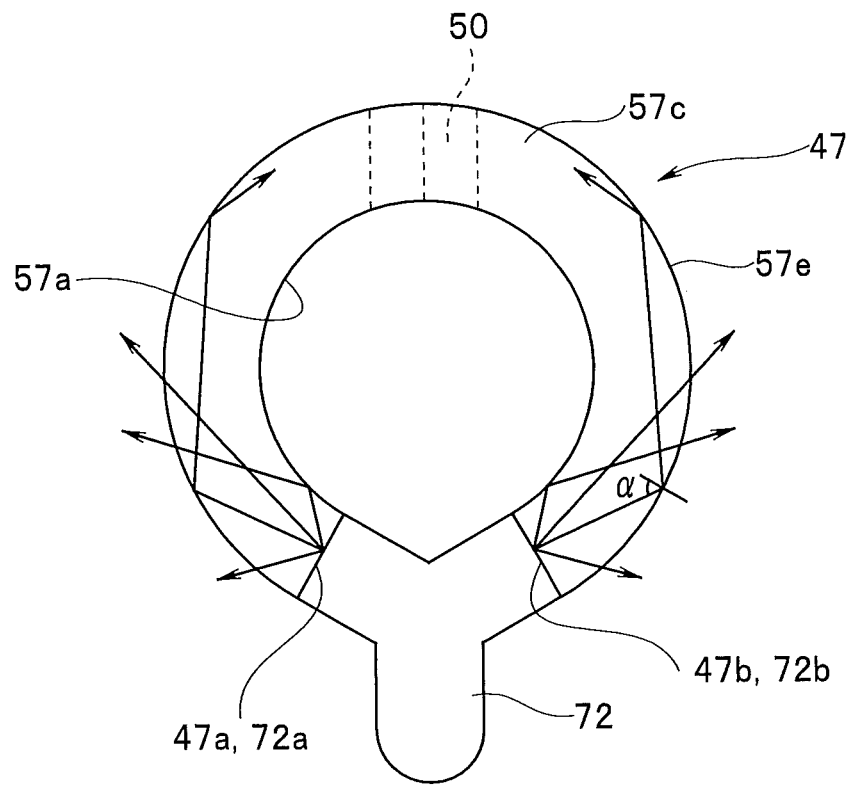
FIG. 14A is a front view illustrating an illumination member.
Figure 14B:
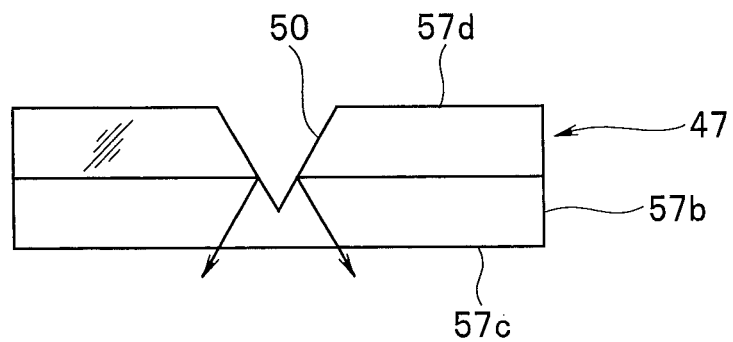
FIG. 14B is a plan view from the top of FIG. 14A.
Figure 14C:
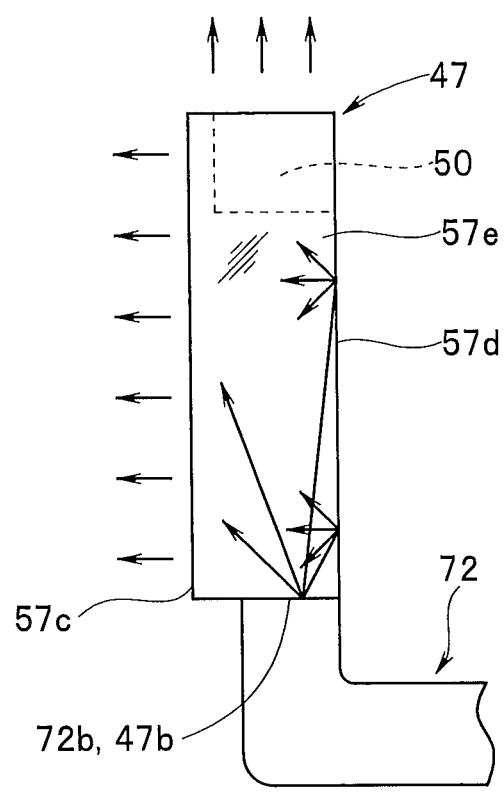
FIG. 14C is a side view from the right side of FIG. 14A.

FIGS. 14A to 14C illustrate an illumination member corresponding to FIG. 8A to FIG. 8C in the first embodiment, respectively.

While in the first embodiment, the reflective surfaces 57a and 57b are provided at the inner circumferential face and the outer circumferential face of the light-guiding plate 47, respectively, in the light-guiding plate 47 according to the present embodiment, a reflective surface 57a is provided at the inner circumferential face and a transmissive surface 57e is provided at the outer circumferential face.

Note that in the present embodiment, a reflective surface 50 is formed by cutting out an area in the vicinity of a position in an upper portion of the light-guiding plate 47 into a wedge shape, and, providing e.g., a metal film for reflection on an end face resulting from the cut-out. The rest of configuration is similar to that of the first embodiment.

Operations of the present embodiment with the configuration as described above have a main difference in that the reflective surface 57b on the outer circumferential face of the light-guiding plate 47 in the first embodiment is replaced with the transmissive surface 57e. Accordingly, an operation according to this difference will be described.

While in the first embodiment, as illustrated in FIG. 8A, light falling on the outer circumferential face is fully reflected toward the inside of the light-guiding plate 47, in the present embodiment, as illustrated in FIG. 14A, light falling on the outer circumferential face at an incident angle α equal to or exceeding a predetermined value is fully reflected. On the other hand, light falling on the outer circumferential face at an incident angle smaller than the predetermined value penetrates the outer circumferential face and exits laterally and serves as side-viewing illuminating light that illuminates the lateral side (observation field of view for side-viewing).

Furthermore, as illustrated in FIG. 14C, light falling on a back face is scattered to a front side or a lateral side (the inner circumferential face or the outer circumferential face) by a scattering reflective surface 57d provided on the back face and exits to an observation field of view for forward-viewing side from the front face or to the observation field of view for side-viewing side from the outer circumferential face.

Also, light guided to the upper side of the light-guiding plate 47 is reflected by the reflective surface 50 as in the first embodiment.

Therefore, according to the present embodiment, forward-viewing illumination and side-viewing illumination can be provided from the forward-viewing/side-viewing illuminating window 71 provided in the light-guiding plate 47, the effects of the first embodiment (effects such as the observation field of view for forward-viewing can be illuminated with reduced illumination unevenness and the distal end portion can be downsized) can be provided, and furthermore, a size in a longitudinal direction of the distal end portion 6 can be reduced.

Besides the above-described embodiments, a configuration resulting from the first embodiment or the second embodiment being modified may be employed.

For example, although in the second embodiment, the light-guiding portion 72 is provided integrally with the light guide 45, the light guide 45 and the light-guiding member 46 may be attached to each other via bonding as in the first embodiment.

Figure 15:
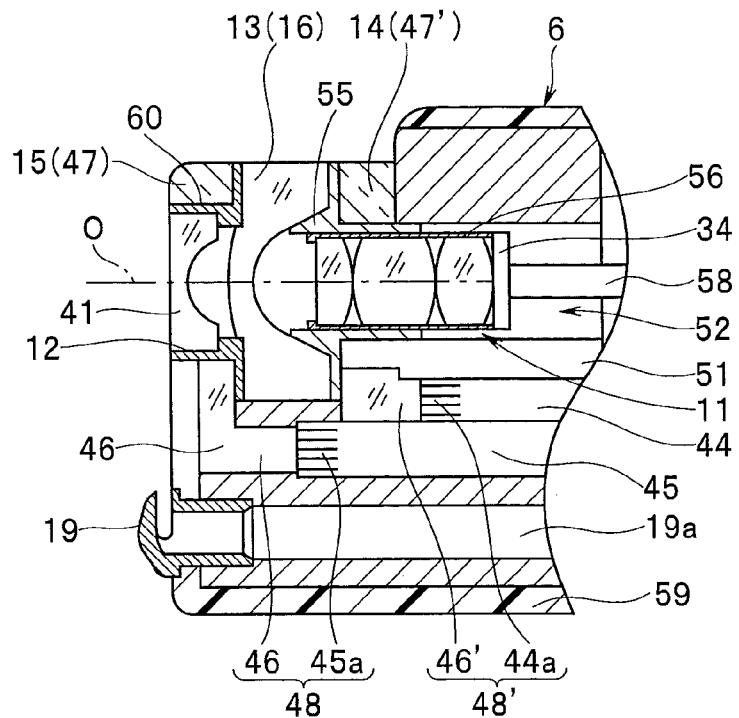
FIG. 15 is a front view of a distal end portion in a modification of the second embodiment.

FIG. 15 illustrates a vertical cross-sectional view of a distal end portion 6 resulting from, for example, the second embodiment being modified. In the first embodiment, side-viewing illumination is provided by means of reflection using a reflective member. However, in the configuration illustrated in FIG. 15, a configuration in which illumination for side-viewing in the configuration of the second embodiment in which illumination for forward-viewing and side-viewing is provided by the C-ring-shaped light-guiding plate 47 is provided separately from illumination for forward-viewing is employed.

Thus, in FIG. 15, a distal end portion of the light guide 44 is fixed by a body portion 51 inside a support member 18 so that the light guide 44 is adjacent to the light guide 45. A distal end face of the light guide 44 guides light from a light source apparatus 31 and makes the light exit, and the exiting light falls on an incident surface of a proximal end of a second light-guiding member 46'.

Accordingly, the distal end portion of the light guide 44 forms a light exit member 44a that makes light guided from the light source apparatus 31 exit.

Light exiting from the distal end face of the light exit member 44a (distal end face of the light guide 44) forward in an axis direction of the distal end portion 6 enters a C-ring-shaped light-guiding plate 47' arranged in a C-ring-shaped side-viewing illuminating window 14 via a light-guiding member 46' molded into an L-shape. Note that an outer circumferential part of the light-guiding plate 47' corresponding to (the rear side of the position of) the lower side of the observation field of view for forward-viewing is also cut off to form incident surfaces 47a' and 47b' as in the case of the light-guiding plate 47. Furthermore, the light-guiding plate 47' has, for example, a predetermined inner diameter that fits on an outer circumferential face of a lens barrel 55, and an outer diameter of the light-guiding plate 47' is, for example, a predetermined outer diameter equal to an outer diameter of a mirror lens 16.

The distal end portion of the light guide 44, which is the light exit member 44a, and the light-guiding member 46' form a light exit portion 48' that emits light so as to fall on the incident surfaces 47a' and 47b' of the light-guiding plate 47'. The light entering the C-ring-shaped second light-guiding plate 47' is made to exit laterally from side-viewing illuminating window 14 as illuminating light.

The second light-guiding member 46' and the second light-guiding plate 47' form a second illumination member 49' that perform side-viewing illumination. Note that FIG. 15 illustrates a structure in which forward-viewing illumination is provided by the light guide 45, the light-guiding member 46 and the light-guiding plate 47 as in case of the first embodiment.

Figure 16:
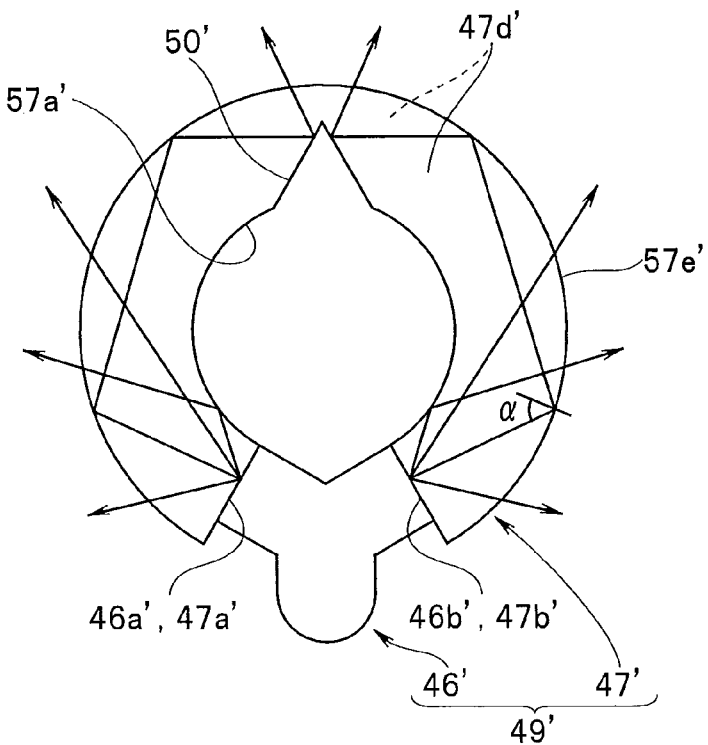
FIG. 16 is a front view illustrating a light-guiding member and a light-guiding plate in FIG. 15.

FIG. 16 illustrates the second illumination member 49'.

As illustrated in FIG. 16, light guided by the light-guiding member 46' falls on the incident surfaces 47a' and 47b' of the C-ring-shaped second light-guiding plate 47' from the exit surfaces 46a' and 46b'. On a front face of the second light-guiding plate 47', a scattering reflective surface 57d' that performs scattering and reflection is provided as in a back face thereof. Also, on an inner circumferential face of the second light-guiding plate 47', a reflective surface 57a' is provided and on an outer circumferential face of the same, a transmissive surface 57e' is provided.

Furthermore, at a position in the vicinity of an upper portion of the second light-guiding plate 47', a reflective surface 50' that performs reflection toward the outer circumference, that is, lateral reflection is provided by an end face resulting from a part of the inner circumferential face of the second light-guiding plate 47' being cut out toward the outer circumferential face into a wedge shape. Light guided to the second light-guiding plate 47' is made to exit laterally from the side-viewing illuminating window 14, that is, illuminating light is made to exit to the observation field of view for side-viewing.

According to the present modification, forward-viewing observation and side-viewing observation can be performed, and at that time, illumination can be provided to the observation field of view for forward-viewing with reduced illumination unevenness, and illumination can be provided to the observation field of view for side-viewing with reduced illumination unevenness, and the distal end portion 6 can be downsized. Accordingly, an observation image facilitating diagnosis can be provided for a surgeon.

Furthermore, where the reflective member for side-viewing illumination in the first embodiment is used, circumferential arrangement of a plurality of distal end faces of the light guide 44 is necessary for performing side-viewing illumination widely in the circumferential direction; however, in the case of the present modification, side-viewing illumination can be performed widely in the circumferential direction by providing a distal end face of the light guide 44 at only one position. Thus, the manufacturing costs can be reduced.

Note that in the case of the present embodiment (including the modification), for example, a structure for making light generated by a light-emitting device such as an LED, which is a light exit member, exit directly so as to fall on the incident surfaces 47a and 47b of the light-guiding plate 47 may be employed without the light-guiding member 46 nor 46' being provided.

(Third Embodiment)

Next, a third embodiment of the present invention will be described. Although the above embodiments, modifications and the like has been described in terms of a configuration where an objective lens system 11 that is available for forward-viewing and side-viewing, the present embodiment is applicable to a case where an objective lens system for forward-viewing is provided.

Figure 17:
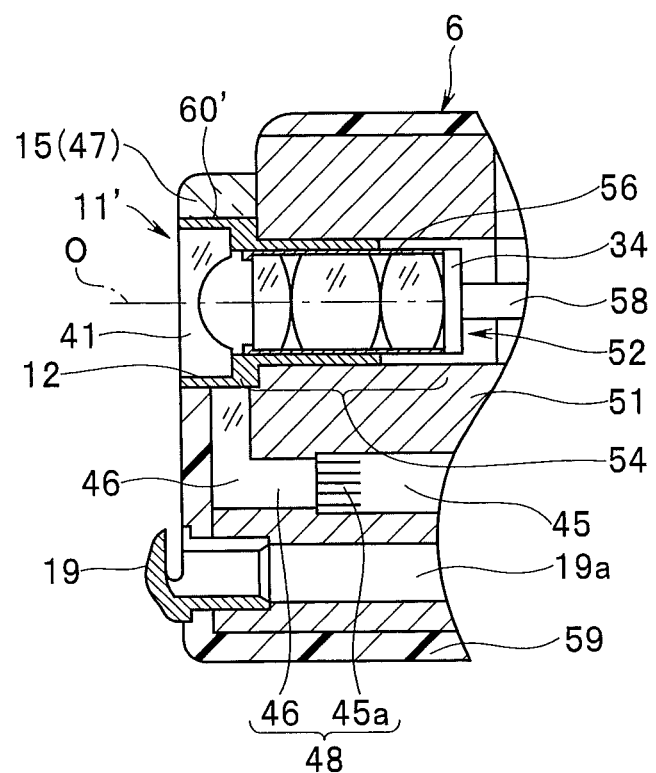
FIG. 17 is a vertical cross-sectional view of a distal end portion in a third embodiment of the present invention.

FIG. 17 illustrates an example structure of a distal end portion 6 including an objective lens system 11' for forward-viewing, according to the third embodiment of the present invention. An endoscope according to the present embodiment is similar to those of the embodiments and modifications described above, and thus, a description will be provided only for a configuration different from those of the embodiments and modifications.

The distal end portion 6 of the endoscope according to the present embodiment employs, for example, the objective lens system 11' having a structure including no mirror lens 16 provided in the side-viewing observation window 13 in FIG. 15, and also employs a structure including no side-viewing observation window 13.

In the present embodiment, a lens barrel 56 with a rear lens portion 54 and an image pickup device 34 attached thereto is fitted into a front lens barrel 60' with a distal end lens 41 attached thereto, and an amount of the fitting in the optical axis O direction is adjusted for focus adjustment. In this case, focus adjustment is made so that an object image for forward-viewing can be formed on an image pickup surface of the image pickup device 34. Also, in the present embodiment, the structure includes no side-viewing illuminating window 14, either.

Thus, the distal end portion 6 illustrated in FIG. 17 has a structure including none of the light guide 44, the second light-guiding member 46' and the second light-guiding plate 47' used for side-viewing illumination in FIG. 15. However, as in the case of illustration in FIG. 15, light guided by the light guide 45 and exiting from a distal end face thereof is guided by the light-guiding member 46, and further illuminating light is made to exit to the field of view for forward-viewing by the C-ring-shaped light-guiding plate 47 provided in the forward-viewing illuminating window 15. Note that the light-guiding member 46 and the light-guiding plate 47 each has a structure that is the same as that described in the first embodiment.

Operations of the present embodiment in terms of forward-viewing illumination are similar to those of the first embodiment, and a description thereof will be omitted.

As described in the first embodiment, the present embodiment can effectively prevent an increase in intensity of illuminating light at a part facing the lower side in the conventional example in FIG. 18, resulting in generation of halation.

Furthermore, since in the present embodiment, the forward-viewing illuminating window 15 is formed on an outer circumference of the forward-viewing observation window 12 in a C-ring shape so as to exclude the lower side part, enabling illumination of the observation field of view for forward-viewing with reduced illumination unevenness. In other words, illumination of good quality can be performed.

Furthermore, according to the present embodiment, the efficiency of use of supplied light for illuminating light actually exiting to an observation field of view can be enhanced by a wedge-shaped reflective surface 50, enabling downsizing of the illumination member 49 as well as downsizing of the distal end portion 6.

According to the present embodiment, compared to the first embodiment, neither the side-viewing observation window 13 nor the side-viewing illuminating window 14 is provided, enabling further reduction in length of the distal end portion 6.

Next, an illumination apparatus for an endoscope that enables even illumination using illuminating light guided by a light guide, is small in size and easy to manufacture, and has a large resistance to deformation will be described.

(Fourth Embodiment)

As illustrated in FIG. 18, an endoscope 101 with the illumination apparatus for an endoscope according to the first embodiment of the present invention installed therein includes an elongated insertion portion 102 to be inserted into, e.g., a body cavity, an operation portion 103 provided at a rear end of the insertion portion 102, and a universal cord 104 extending out from the operation portion 103. A light source connector and a signal connector at a non-illustrated terminal of the universal cord 104 are connected to a light source apparatus and a processor that performs signal processing, respectively, which are external to the endoscope 101.

The insertion portion 102 having flexibility includes a distal end portion 106 provided at a distal end thereof, and a bendable bending portion 107 provided adjacent to a rear end of the distal end portion 106. The bending portion 107 can be bent in arbitrary bending directions, upward, downward, rightward and leftward by a user performing an operation to rotate a bending operation knob 105 provided at the operation portion 103 via a finger of the user's hand grasping the operation portion 103.

The light source apparatus generates illuminating light and the illuminating light enters the light source connector for the endoscope 101.

Illuminating light entering the light source connector is guided to a distal end face of a light guide 108 by the light guide 108 inserted inside the universal cord 104, the operation portion 103 and the insertion portion 102. Illuminating light guided to the distal end face of the light guide 108 by the light guide 108 enters an annular-shaped light-guiding body 112 included in the illumination apparatus 111 for an endoscope according to the fourth embodiment. Then, illuminating light exits from an illuminating light exit surface (abbreviated as exit surface) 131 at a front face of the light-guiding body 112 to illuminate a site to be observed side such as a diseased part in a body cavity to which the insertion portion 102 is inserted, as an illumination range.

Figure 19:
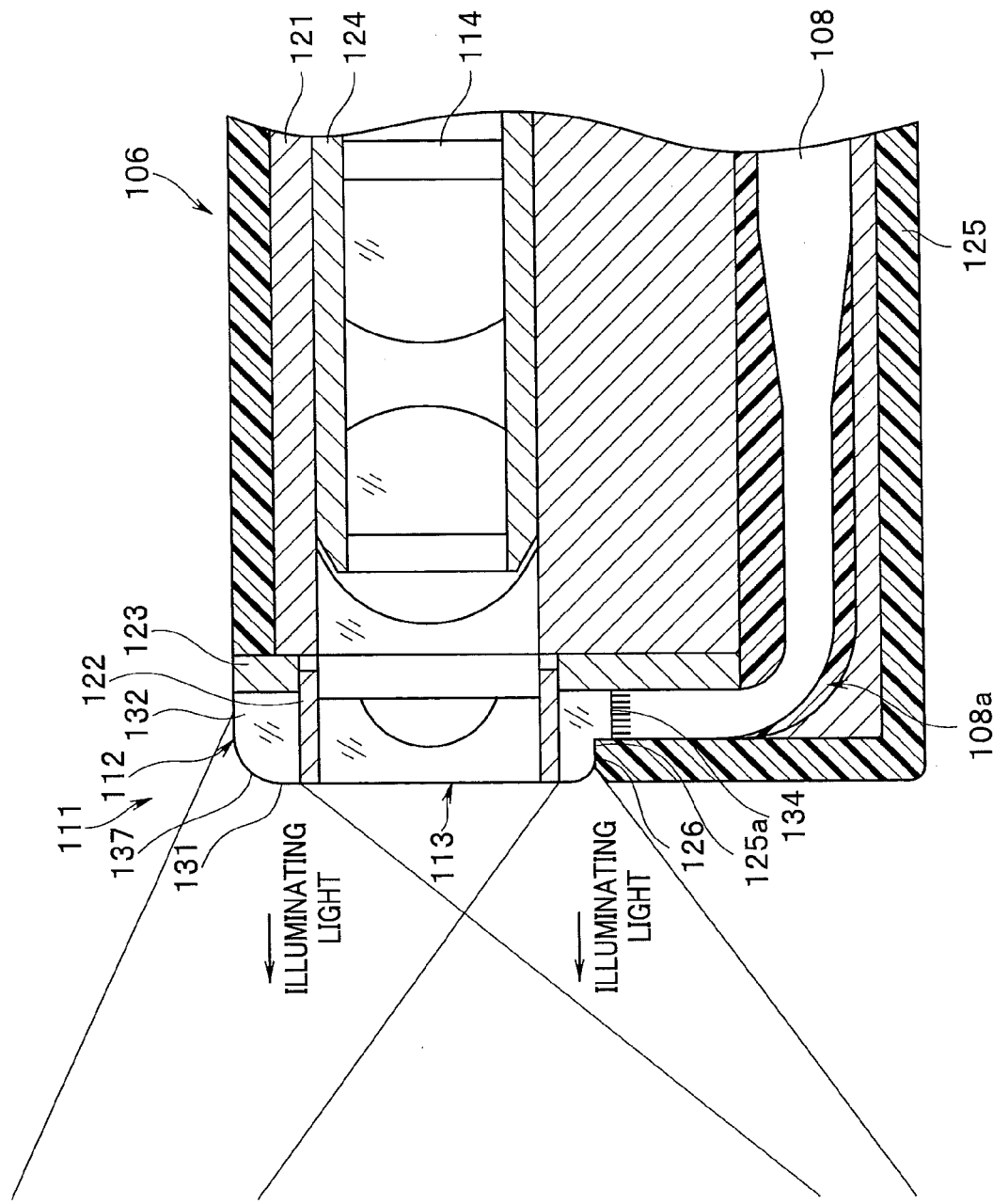
FIG. 19 is a vertical cross-sectional diagram illustrating a configuration of a part around a distal end portion of the endoscope in FIG. 18.

Furthermore, as illustrated also in the cross-sectional view of the distal end portion 106 in FIG. 19, an objective optical system 113 is arranged inside the annular-shaped light-guiding body 112, and at a position where an image from the objective optical system 113 is formed, an image pickup device 114 including, e.g., a charge-coupled device is arranged.

The objective optical system 113 forms an optical image of the illuminated site to be observed on an image pickup surface of the image pickup device 114, and an image pickup signal subjected to photoelectric conversion by the image pickup device 114 is inputted to the processor via a signal cable. The processor performs signal processing on the image pickup signal and outputs the resulting image signal to a display apparatus, and the display apparatus displays an endoscopic image corresponding to the image signal.

Also, as illustrated in FIG. 18, in the vicinity of a front end of the operation portion 103, a treatment instrument insertion port 115 for inserting a treatment instrument thereto is provided, and the inside of the treatment instrument insertion port 115 communicates with a channel formed along a longitudinal direction of the insertion portion 102. The channel opens as a channel distal end opening portion 116 at a distal end face of the distal end portion 106.

As illustrated in FIG. 19, in the distal end portion 106, a distal end of a through-hole for observation (image pickup) provided in a columnar distal end constituent member 121 is cut out so as to have an increased diameter, an annular-shaped light-guiding body 112 is arranged on the outer circumferential side of a distal end lens barrel 122 (including a light-blocking member), and a distal end lens in an objective optical system 113 attached to the distal end lens barrel 122 is arranged on the inside of the annular inside of the light-guiding body 112. As described above, at the position where an image from the objective optical system 113 is formed, the image pickup device 114 is arranged. Note that the distal end lens barrel 122 is fixed as a result of being fitted into a hole portion of a holding plate 123 arranged at a back face of the light-guiding body 112, the holding plate 123 being formed using, e.g., a stainless steel, and the holding plate 123 is fixed to a distal end face of the distal end constituent member 121.

A rear lens group arranged behind the distal end lens included in the objective optical system 113 is attached to a lens barrel 124.

Furthermore, in a through-hole for illumination provided in the distal end constituent member 121 provided along a longitudinal direction of the insertion portion 102, the distal end side of the light guide 108 is inserted, and at the distal end side of the through-hole, the light guide 108 is flexed at an angle of substantially 90°. Note that the light guide 108 includes a fiber bundle resulting from numerous light guide fibers for conveying illuminating light being bundled.

In FIG. 19, a distal end of the flexed light guide 108 is made to extend out to the light-guiding body 112 provided thereabove. Illuminating light exiting from an end face of the flexed distal end enters an incident portion (or a light-receiving section) formed in the light-guiding body 112, which is in contact with the end face.

Also, an outer circumferential face of the distal end constituent member 121 is covered by a distal end cover 125 and the flexed distal end side of the light guide 108 is covered by the distal end cover 125, thereby protecting the light guide 108.

Furthermore, a notch portion 126 resulting from a part in the vicinity of a lower end of an exit surface 131 of the light-guiding body 112 being cut out to form a stepped shape is provided, and at the distal end cover 125, a projection portion 125a projecting so as to abut to the notch portion 126 is formed. Then, the projection portion 125a protects the light-guiding body 112 so as not to come off from the distal end portion 106. Also, the light guide 108 is covered by a protection tube inside the insertion portion 102, and inside the distal end portion 106, is fixed to the through-hole for illumination via, e.g., a filling member or an adhesive.

Illuminating light entering the light-guiding body 112 from the distal end face of the light guide 108 is made to exit from the exit surface 131 provided on the front face side of the light-guiding body 112, and substantially evenly illuminates an observation range for the observation objective optical system 113. In FIG. 19, schematic areas of illuminating light from the exit surface 131 are illustrated.

Figure 20A:
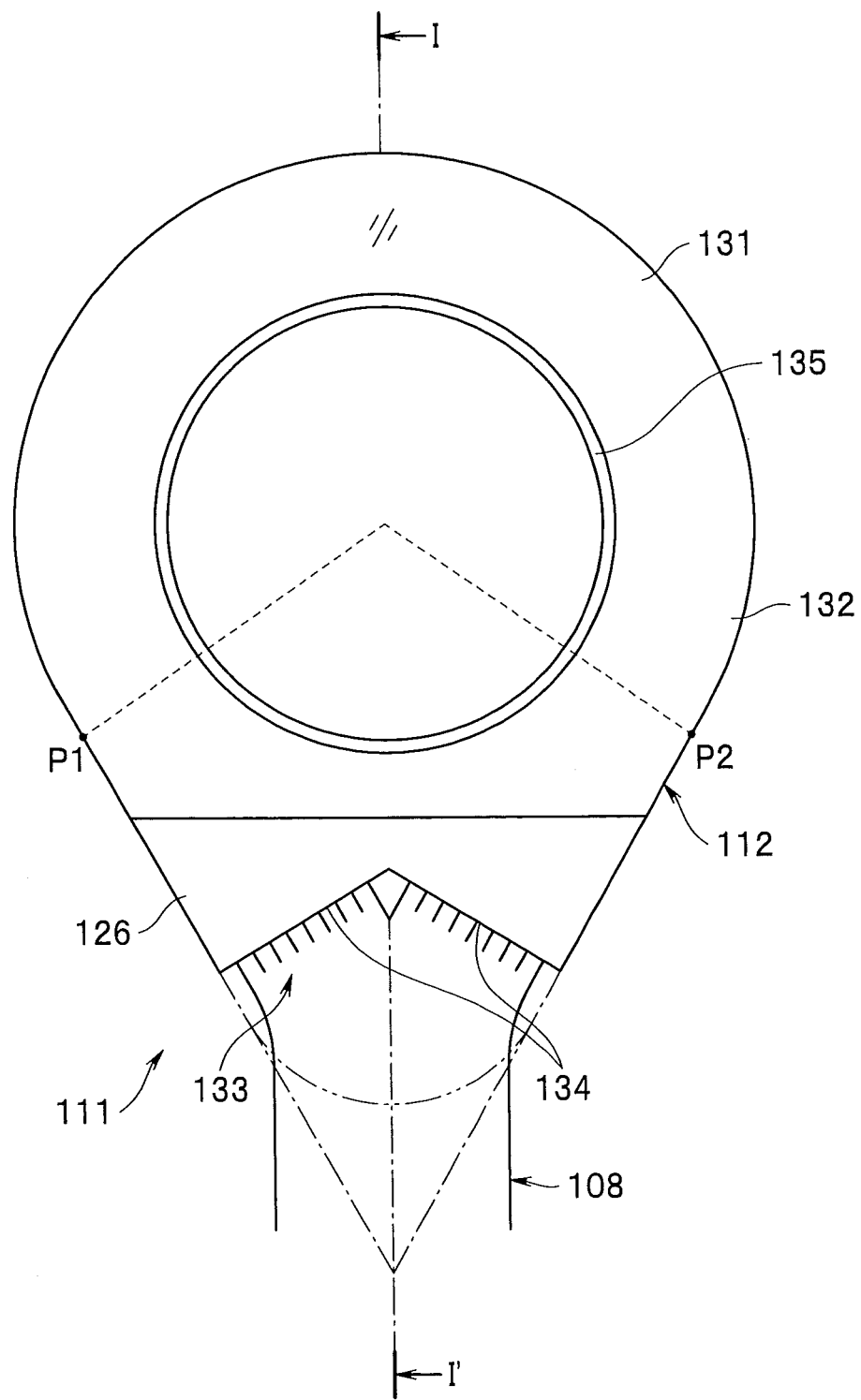
FIG. 20A is a front view of an illumination apparatus for an endoscope as viewed from the front side of a light-guiding body.
Figure 20B:
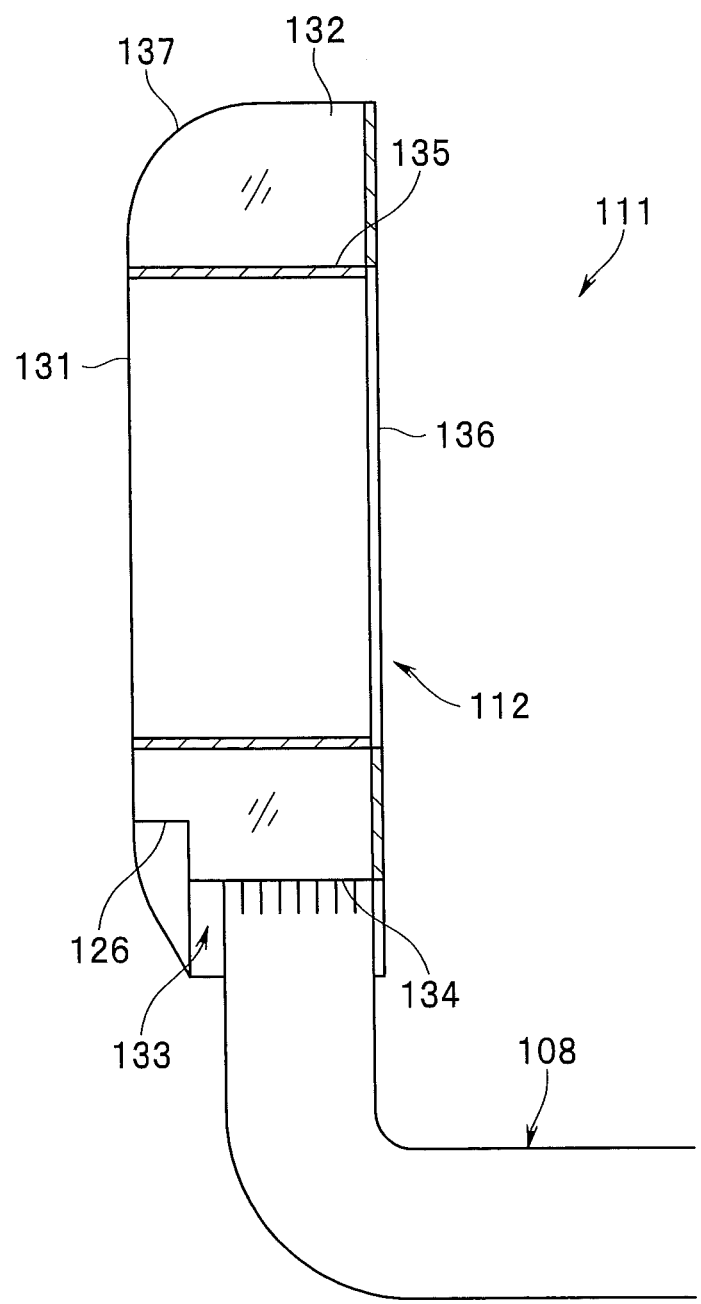
FIG. 20B is a cross-sectional view taken along line I-I' in FIG. 20A.

FIG. 20A illustrates a front view of the illumination apparatus 111 for an endoscope according to the present embodiment as viewed from the exit surface side of the light-guiding body 112, and FIG. 20B illustrates a cross-sectional diagram taken along line I-I' in FIG. 20A.

As illustrated FIG. 20A, the illumination apparatus 111 for an endoscope is formed using an annular and transparent light-guiding body 112. The illumination apparatus 111 for an endoscope has an outer shape that is a substantial droplet shape touched by each of two lines, which are indicated by alternate long and short dash lines, extending from two points P1 and P2 forming an angle smaller than an angle (of 180°) formed by two points along a diameter of the annular outer circumference, as a cross-sectional shape of the light-guiding body 112 as viewed from the front side.

Furthermore, the illumination apparatus 111 for an endoscope includes an annular portion 132 formed with a notch portion 133 provided therein, the notch portion 133 resulting from a part of the outer circumferential side, more specifically, a portion in the periphery of positions touched by the two lines on the outer shape that is the droplet shape, the portion including such positions, being cut out in directions substantially normal to the respective two lines so that the annular-shape is not disconnected (connected annular-shape is formed). Note that the shape illustrated in FIG. 20A is the same in a cross-sectional diagram parallel to the surface of the sheet of FIG. 20A (however, the notch portion 126 may not appear depending on the position of the cross-section).

Also, in the illumination apparatus 111 for an endoscope, the light-guiding body 112 is provided with two cut surfaces of the notch portion 133 and respective incident end faces 134 forming an incident portion (or light-receiving portion), which are in contact with end faces of the light guide 108, are provided at the respective cut surfaces so that illuminating light from the light guide 108 perpendicularly falls on the respective cut surfaces.

The incident end faces 134 may be entire regions of the respective two cut surfaces formed as a result of the cut-off to form the notch portion 133, or may be formed by (parts of) respective two end face regions that are in contact with the respective end faces of the light guide 108.

Also, in the vicinity of the distal end of the light guide 108, as illustrated in FIG. 20A, the light guide 108 is branched so as to form a Y-shape and the two end faces resulting from the branching contact the two respective incident end faces 134. In this case, directions in which the fibers run in the vicinity of the end faces of the light guide 108 are perpendicular to the respective incident end faces 134 and in such state, the fibers contact the respective incident end faces 134. Then, settings are made so that illuminating light from the light guide 108 enters (falls on the two incident end faces 134) in the directions perpendicular to the two respective incident end faces 134. As described above, in the present embodiment, a function that makes illuminating light guided by the light guide 108 enter in the directions perpendicular to the two respective incident end faces 134 simultaneously is provided.

Also, in the illumination apparatus 111 for an endoscope, a reflective material 135 is provided in a thin-film shape with an inner circumferential face (inner circumferential surface) of the annular-shaped annular portion 132 of the light-guiding body 112, the reflective material 135 including a member having a high reflectivity to illuminating light such as aluminum, and having a function as a reflective portion that when illuminating light entering the inside of the light-guiding body 112 falls on the inner circumferential face, reflects the light toward the inside of the annular portion 132.

The reflective material 135 includes a reflective surface that serves as a surface that reflects the illuminating light falling on the inner circumferential face from the inside of the annular portion 132 toward the inside of the annular portion.

Note that the reflective material 135 forming the reflective portion is limited to a case where the reflective material 135 is provided on the entire inner circumferential face of the annular portion 132 and the reflective material 135 may be one that is arranged at least on the incident portion side where the notch portion 133 is provided (part of the inner circumferential face close to the light guide 108 at the lower end in FIG. 20A) and when illuminating light entering the light-guiding body 112 directly falls on the inner circumferential face, reflects the light to the inside of the annular portion 132. As described above, where the reflective material 135 is provided at the part close to the incident end faces 134 where the notch portion 133 is provided, a part of the inner circumferential face other than that part may be provided with a light-blocking portion to prevent illuminating light from entering the objective optical system 113.

Note that since in the present embodiment, the annular-shaped distal end lens barrel 122 including a material having a function that blocks light is arranged inside the annular portion 132, even if illuminating light exits to the inside of the inner circumferential face of the annular portion 132, the light is blocked by the distal end lens barrel 122, enabling the illuminating light to be prevented from entering (the distal end lens in) the objective optical system 113 inside the distal end lens barrel 122. Thus, it is not necessary to provide a light-blocking portion on the inner circumferential face of the annular portion 132.

Furthermore, in the illumination apparatus 111 for an endoscope, an exit surface 131 that makes illuminating light entering the inside of the annular portion 132 of the light-guiding body 112 from the light guide 108 exit is provided on one of two annular surfaces of the annular portion 132 formed by the light-guiding body 112, the two annular surfaces facing each other.

Note that a substantial droplet shape of the annular portion 132 before provision of the notch portion 133 is not limited to the shape indicated by in the alternate long and short dash lines in FIG. 20A and may be a shape having a rounded lower end as indicated by the alternate long and two short dashes line. With any of the shapes, the substantial droplet shape is the same after provision of the notch portion 133 in the annular portion 132.

Also, as illustrated in FIG. 20B, on an annular surface on the back side opposite to the exit surface 131 of the annular portion 132 of the light-guiding body 112, a light diffusion portion 136 that diffuses illuminating light entering from the inside of the annular portion 132 so as to exit in directions each having an angle relative to a direction perpendicular to the annular surface of the annular portion 132 to reflect the light toward the inside of the annular portion 132 is provided. Note that the light diffusion portion 136 may include a light scattering portion that scatters incoming illuminating light mainly to the inside of the annular portion 132.

Furthermore, the light diffusion portion 136 may be formed by, for example, making the annular surface on the back side be a roughened surface so as to be a satin-finish coarse surface, and the roughened surface may further be coated with a coating material such as a reflective paint having a high function that reflects light. Note that as in the later-described modification, the annular surface on the back side may be a hemispherically-roughened surface.

Furthermore, in the present embodiment, the exit surface 131 of the annular portion 132 is processed so as to be a curved surface 137 having a rounded outer circumference as illustrated in FIG. 20B.

As described above, the curved surface 137 formed on the outer circumferential side, which is a part of the exit surface 131 of the annular portion 132, has a function as a light spreading portion that makes illuminating light falling on the curved surface 137 exit in a spread manner in directions each having an arbitrary angle relative to a direction perpendicular to the annular surface (thus, in the wider sense, a function as a light diffusion portion that diffuses light in directions each having an angle relative to the direction perpendicular to the annular surface).

Figure 21A:
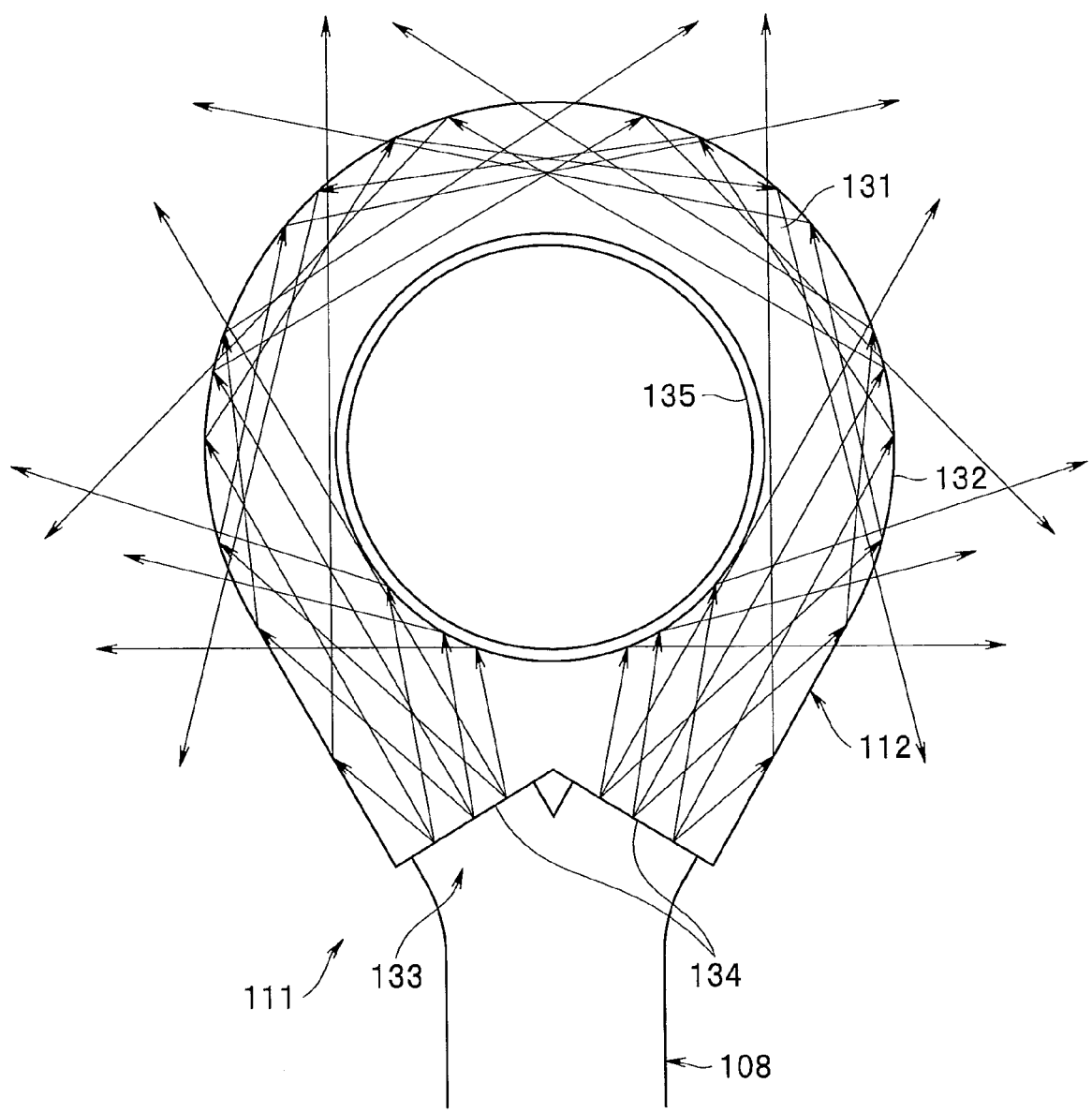
FIG. 21A is a diagram illustrating a manner in which illuminating light entering a light-guiding body is guided using a front view.
Figure 22A:
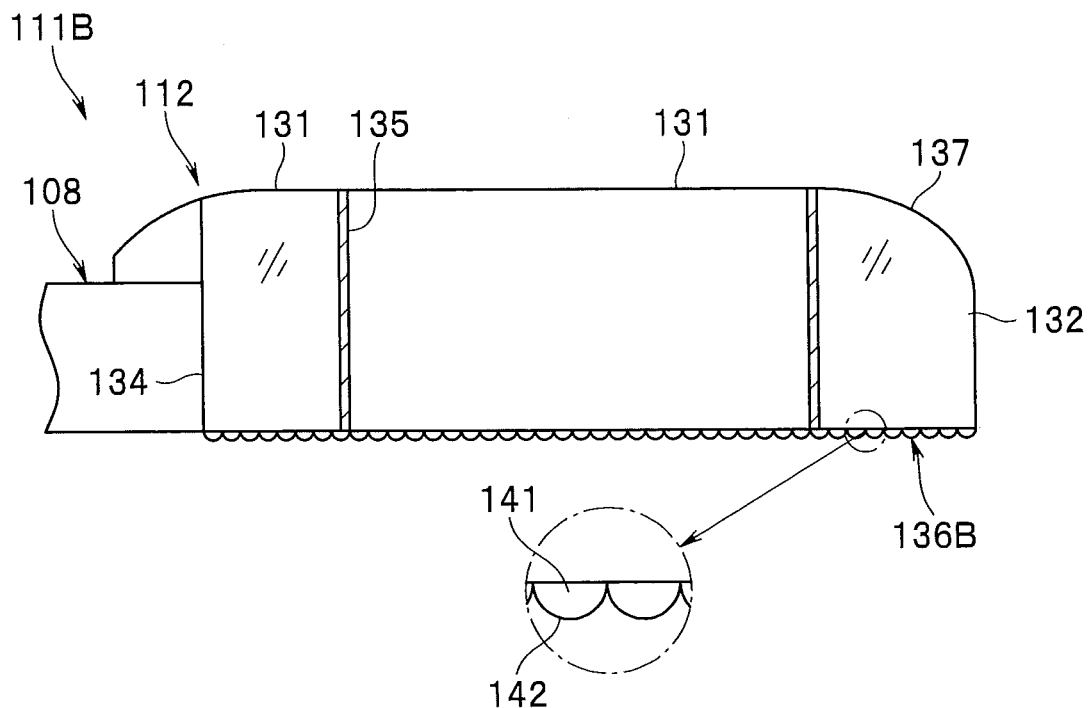
FIG. 22A is a cross-sectional side view of an illumination apparatus for an endoscope in a second modification of the fourth embodiment.
Figure 22B:
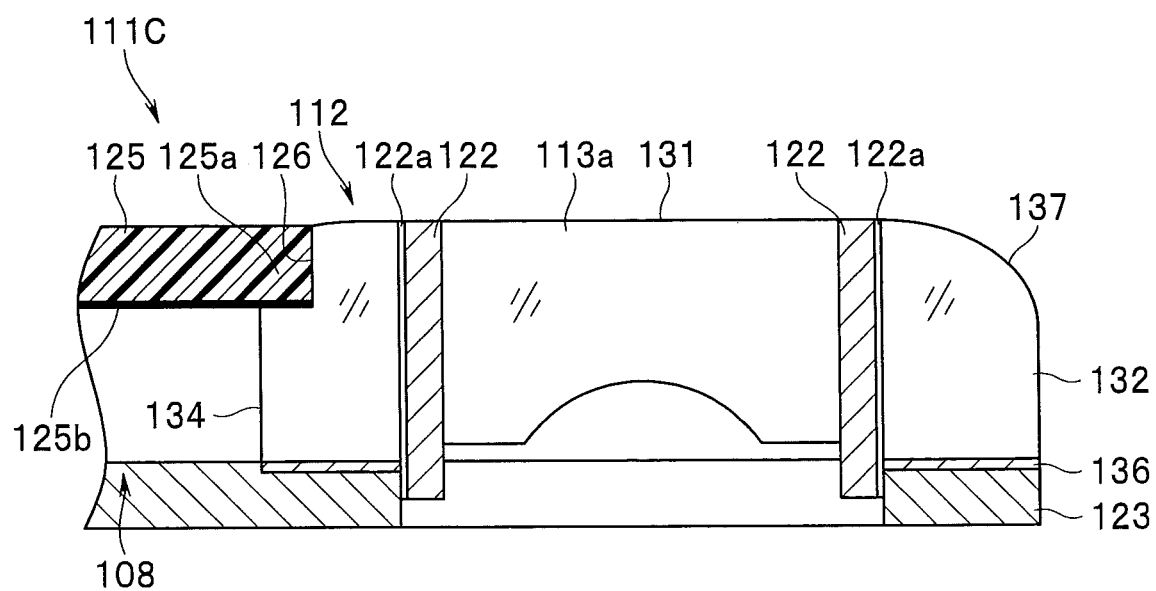
FIG. 22B is a cross-sectional side view of an illumination apparatus for an endoscope in a third modification of the fourth embodiment.
Figure 32:
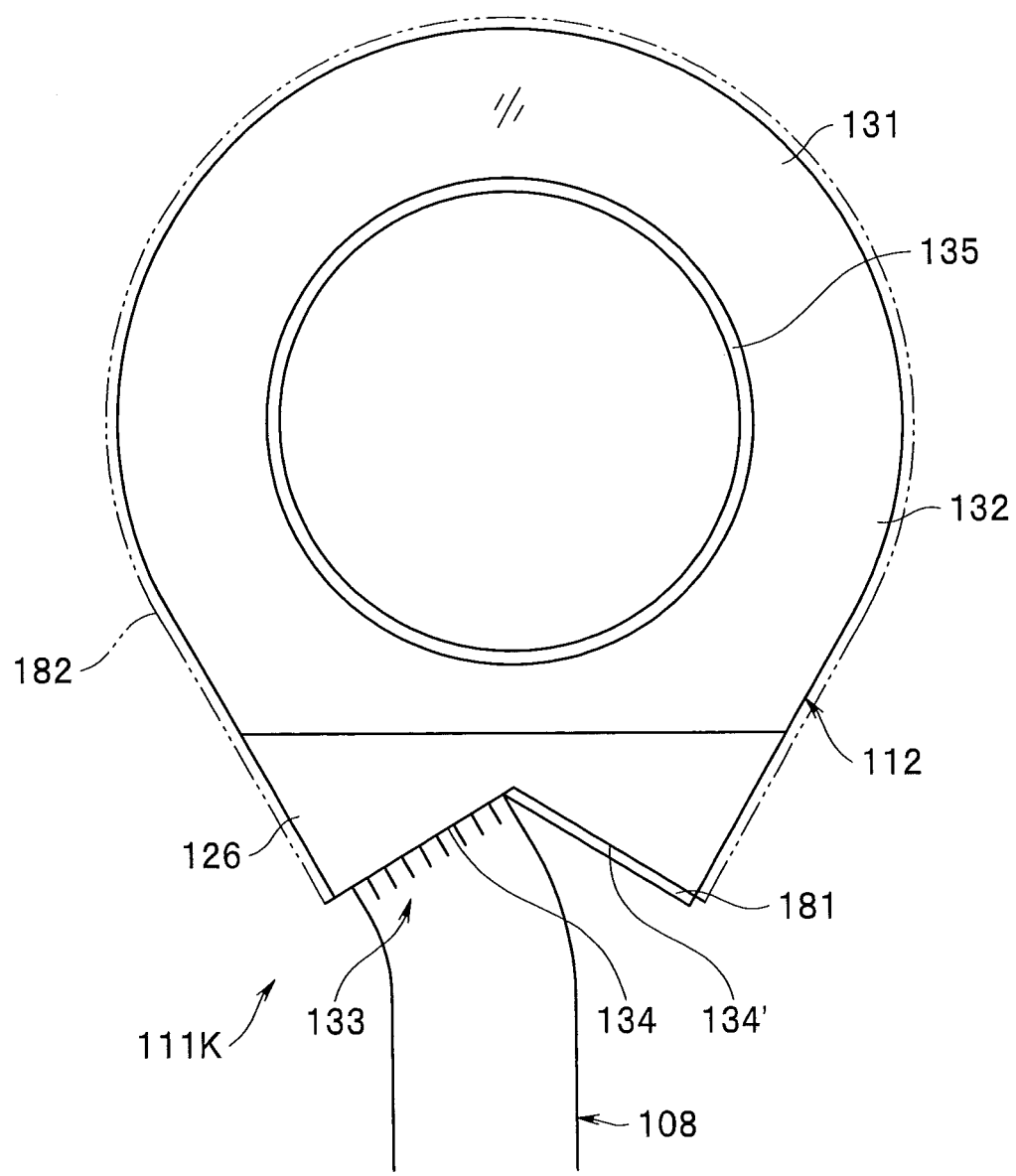
FIG. 32 is a front view of an illumination apparatus for an endoscope including one incident end face.

Note that although FIGS. 20A and 20B each illustrate the notch portion 126, FIG. 21A onwards provide diagrams simplified by omission of the notch portion 126 except FIGS. 22B and 32.

The illumination apparatus 111 for an endoscope according to the present embodiment having the above-described configuration is an illumination apparatus for an endoscope that makes illuminating light externally entering the transparent light-guiding body 112 including an annular shape via the light guide 108 exit from the light-guiding body 112, the light-guiding body 112 including: an annular portion 132 provided with the notch portion 133 formed by a part of an outer shape that is a substantial droplet shape each of two lines extending from two points on an outer circumference of a circle touches in a cross-section being cut out in directions in which respective lines substantially normal to the two lines are connected and the annular shape is not disconnected; the incident end faces 134 provided at the cut surfaces resulting from the cut-out in the notch portion 133, the incident end faces 134 forming an incident portion that is in contact with the end faces of the light guide 108 so as to make the illuminating light from the light guide 108 perpendicularly fall on the cut surfaces; the reflective material 135 arranged at least on the side of the inner circumferential face of the annular portion 132 where the notch portion 133 is provided, the reflective material 135 forming a reflective portion that reflects the illuminating light entering the light-guiding body 112 to the inside of the annular portion 132; and the exit surface 131 provided at one of the annular surfaces of the annular portion 132, the exit surface 131 making the entering illuminating light exit.

Next, an operation of the present embodiment will be described. The endoscope 101 illustrated in FIG. 18 is connected to, e.g., the light source apparatus external to the endoscope 101, and the light source apparatus is powered on to generate illuminating light. The illuminating light falls on the incident end faces of the light guide 108, and the light guide 108 guides the entering illuminating light to the end faces at the distal end of the light guide 108.

The end faces of the distal end of the light guide 108 are in contact with the incident end faces 134 of the light-guiding body 112 and are arranged so as to allow illuminating light from the light guide 108 to perpendicularly fall on the incident end faces 134, whereby the illuminating light from the light guide 108 efficiently enters the inside of the annular portion 132 of the light-guiding body 112 (with occurrence of reflection in non-perpendicular directions suppressed).

Figure 21B:
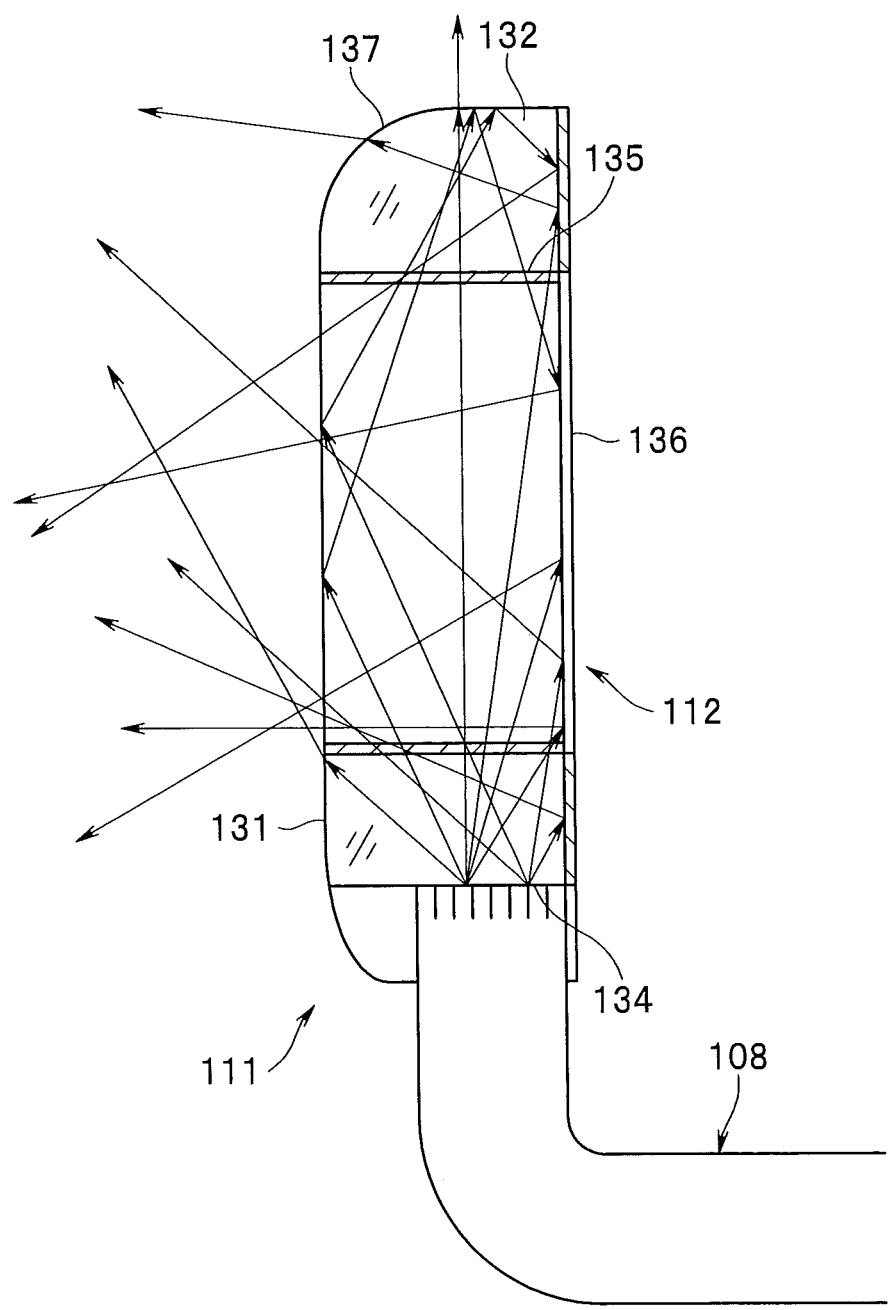
FIG. 21B is a diagram illustrating a manner in which illuminating light entering light-guiding body is guided using a cross-sectional view.

The illuminating light entering the inside of the annular portion 132 of the light-guiding body 112 efficiently exits from the exit surface 131 by means of reflection and light diffusion as in FIGS. 19, 21A and 21B.

As illustrated in FIG. 19, in the present embodiment, the annular portion 132 of the light-guiding body 112 having an annular shape is arranged so as to surround a periphery of the objective optical system 113, and thus, illuminating light guided by the light guide 108 can be made to exit from the exit surface 131 of the annular portion 132 of the light-guiding body 112 so as to substantially evenly illuminate the observation range (image pickup range) for the objective optical system 113. Furthermore, a configuration that exits illuminating light from the exit surface 131 without using an illumination lens (in other words, the annular portion 132 of the light-guiding body 112 doubles as a function of an illumination lens), enabling provision of an illumination apparatus for an endoscope enabling downsizing of a distal end portion 106.

Furthermore, in the present embodiment, the incident end faces 134 are formed by a part of the outer circumferential side of the light-guiding body 112 being cut out so as to maintain (hold) the light-guiding body 112 in a (non-disconnected) annularly-connected shape, and thus, an illumination apparatus for an endoscope that has an enhanced resistance to deformation and is hardly broken when the illumination apparatus is manufactured and thus easy to manufacture can be provided compared to a case of a shape in which the annular shape is disconnected.

Furthermore, as indicated by arrows in FIG. 21A, illuminating light entering the inside of the annular portion 132 of the light-guiding body 112 is reflected by the reflective material 135 on the inner circumferential side of the annular portion 132 and a majority of the illuminating light is reflected by the outer circumferential face of the annular portion 132. Accordingly, the illuminating light entering the light-guiding body 112 can be guided so as to efficiently exit from the exit surface 131.

Furthermore, as illustrated in FIG. 21B, illuminating light entering the inside of the annular portion 132 of the light-guiding body 112 and falling on the back surface from the inside of the annular portion 132 is diffused by the light diffusion portion 136 at the back face of the annular portion 132 in directions each having an angle relative to a direction perpendicular to the annular surface of the annular portion 132, thereby reflecting the light to the inside of the annular portion 132. Accordingly, illuminating light entering the annular portion 132 of the light-guiding body 112 can be guided to efficiently exit from the exit surface 131.

FIG. 21C is a diagram illustrating an operation where a curved surface 137 is formed at a part of the exit surface 131. In the left-side diagram in FIG. 21C, a manner in which light is made to exit by the annular portion 132 of the light-guiding body 112 where no curved surface 137 is formed is indicated by arrows.

In this case, if the angle of incidence on the exit surface 131 from the inside of the annular portion 132 is large, light may be reflected by the exit surface 131, resulting in illuminating light exiting toward the back face which is opposite to the exit surface 131. In other words, a case where illuminating light may largely be deviated from the observation range for the objective optical system 113 occurs, resulting in performing illumination in unnecessary directions.

On the other hand, formation of the curved surface 137 as illustrated in the right side of FIG. 21C enables prevention (suppression) of illuminating light exiting toward the back face, thereby increasing an amount of illuminating light that illuminates the observation range as an illumination range, and also enables exiting light to be spread to illuminate the illumination range with more even light distribution characteristics.

Figure 21D:
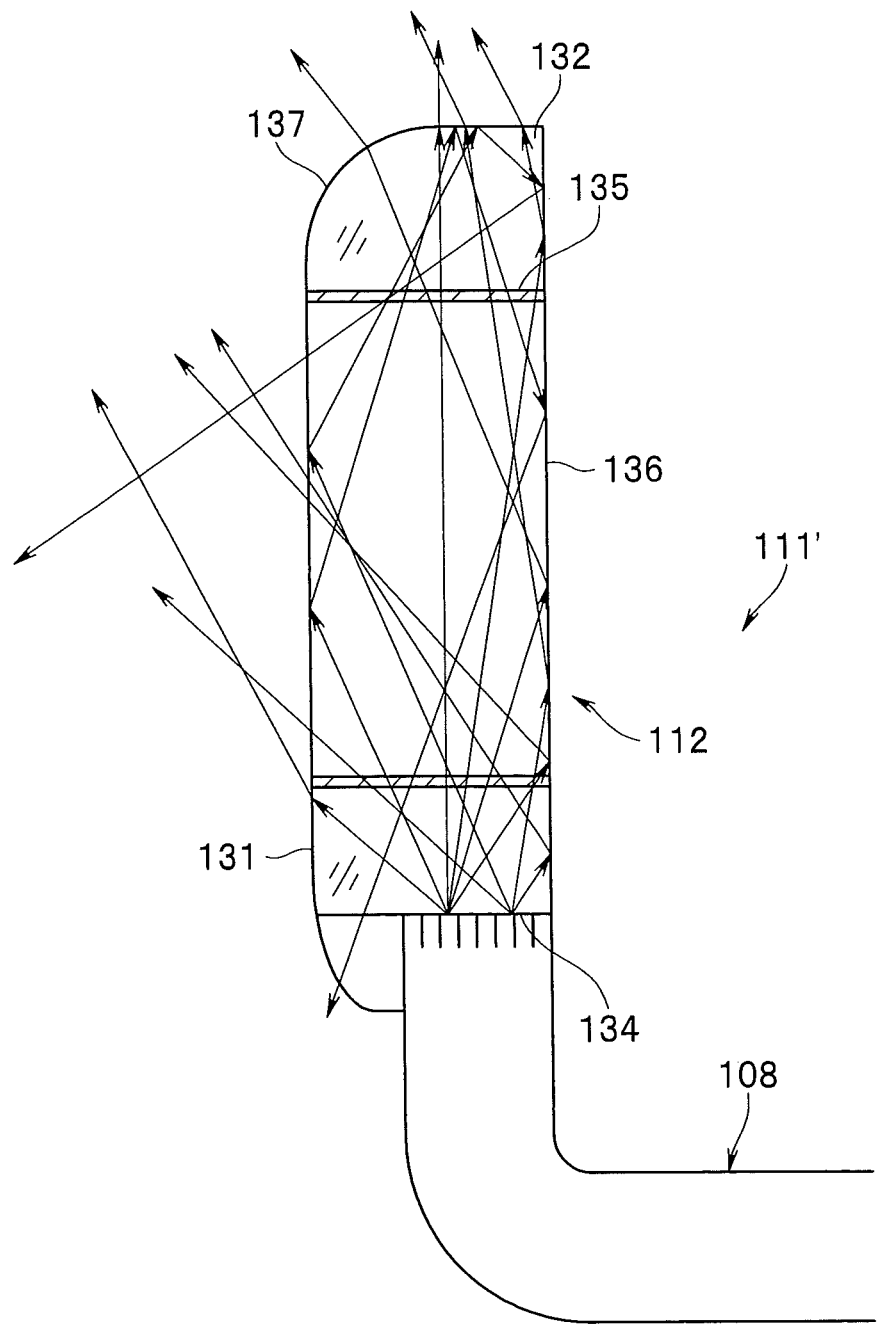
FIG. 21D includes a cross-sectional side view of an illumination apparatus for an endoscope in a first modification of the fourth embodiment and a diagram illustrating a manner in which illuminating light is guided.

Note that in the above fourth embodiment, an illumination apparatus 111' for an endoscope having a configuration according to a first modification in which no light diffusion portion 136 is provided on the back side of an annular portion 132 may be employed. FIG. 21D illustrates a manner in which illuminating light entering a light-guiding body 112 exits from an exit surface 131 in the configuration of the modification.

Since in the present modification, no light diffusion portion 136 is provided, the function that optically diffuses illuminating light falling on the back face of the annular portion 132 is lowered compared to the case of FIG. 21B, and where a wide angle of illumination is provided, such configuration may be employed.

FIG. 22A illustrates a structure of a light diffusion portion 136B in an illumination apparatus 111B for an endoscope according to a second modification of the present embodiment. In the fourth embodiment, for the light diffusion portion 136, for example, the back-side annular surface is made to be a satin-finish roughened surface or the roughened surface is further coated with, e.g., a high reflective paint having a high reflective function.

On the other hand, in the present modification, as an roughened surface of the light diffusion portion 136, hemispherical light diffusion surfaces 141 are formed on a back-side annular surface as illustrated in a partial enlarged illustration in FIG. 22A, and surfaces of the hemispherical light diffusion surfaces 141 are mirror-coated by a mirror-coating portion (or a light-reflective coating portion) 142 to form a light diffusion portion 136B. The rest of the configuration is similar to that of the fourth embodiment. Note that where a function that diffuses or scatters illuminating light falling on the light diffusion surface 141 from the inside of the annular portion 132 to the inside of the annular portion 132 can sufficiently be achieved only by the light diffusion surface 141, a structure with no mirror coating portion 142 is provided may be employed.

The present modification has operations and effects almost similar to those of the fourth embodiment.

Also, FIG. 22B illustrates a structure of a reflective portion provided on an inner circumferential face of an annular portion 132 in an illumination apparatus 111C for an endoscope according to a third modification.

In the fourth embodiment, the reflective material 135 having a function as a reflective portion is provided on the inner circumferential face of the annular portion 132. On the other hand, in the present modification, a reflective surface 122a that includes, e.g., a reflective film and has a high reflection function is provided on an outer surface of an annular-shaped distal end lens barrel 122 with a distal end lens 113a included in an objective optical system 113 attached thereto, to provide a function of the reflective material 135 by means of the reflective surface 122a.

The reflective surface 122a is fitted on an inner circumferential face of an annular portion 132, and illuminating light falling on the reflective surface 122a side from the annular portion 132 of a light-guiding body 112 is reflected by the reflective surface 122a to the inside of the annular portion 132. The rest of the configuration is similar to that of the fourth embodiment. The present modification provides operation and effects almost similar to those of the fourth embodiment. Note that the present modification is not limited to a case where the reflective surface 122a is formed on the entire inner circumferential face of the annular portion 132 and may be provided on a part of the inner circumferential face close to incident end faces 134 forming an incident portion from which illuminating light from a light guide 108 enters.

Note that as described with reference to FIG. 19, a projection portion 125a of a distal end cover 125 abuts to a notch portion 126 having a stepped shape, which is formed in the vicinity of the incident end faces 134 of the annular portion 132 of the light-guiding body 112 as illustrated in FIG. 22B, to protect the light-guiding body 112 from coming off from the distal end portion 106 of the endoscope 101.

In this case, e.g., a light-reflective portion that reflects light may be formed on an inner face of the distal end cover 125 covering a part in the vicinity of a distal end of the light guide 108, together with the projection portion 125a abutting to the notch portion 126 of the annular portion 132. In the example illustrated in FIG. 22B, a light-reflective member or a light-reflective coating portion (mirror-coating portion) 125b may be provided on the inner face of the distal end cover 125 covering the part in the vicinity of the distal end of the light guide 108 to reflect illuminating light leaking to the distal end cover 125 side from the light guide 108 to the light guide 108 side, thereby making illuminating light enter the inside of the light-guiding body 112 from the light guide 108 with a reduced loss in light amount.

Figure 23:
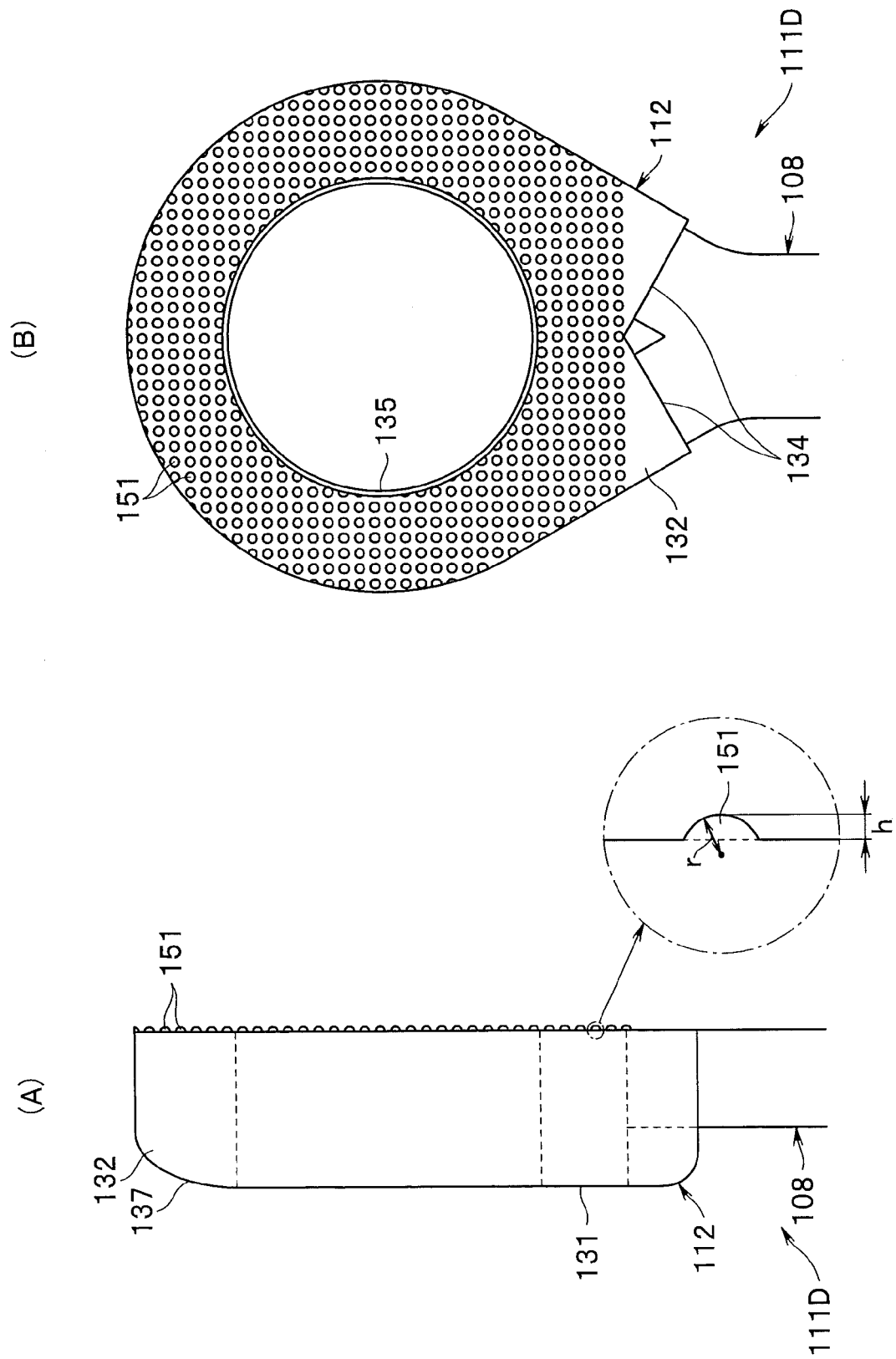
FIG. 23 includes a side view and a back view of an illumination apparatus for an endoscope in a fourth modification of the fourth embodiment.

FIG. 23 includes a structure of each of a side view (A) and a back view (B) of a structure of an illumination apparatus 111D for an endoscope according to a fourth modification of the fourth embodiment. As illustrated in FIGS. 23(A) and 23(B), a substantially hemispherical reflector 151 is formed at, for example, each lattice position on a surface of the back side of an annular portion 132 of a light-guiding body 112 to provide a light diffusion portion. Note that the reflectors 151 may be provided on the entire surface of the back side of the annular portion 132 or as illustrated in FIG. 23, may be provided so as not to be formed in the vicinity of incident end faces 134.

Also, in the present modification, as illustrated in the enlarged diagram with a part enlarged in FIG. 23(A), where r is a curvature radius of the spherical surface, h is a height projecting from the surface of the back side, the reflectors 151 are each set so that the height (h) satisfies expression (1) below, $$h \leq 100 \, \mu m \quad (1), \text{ and}$$

the condition of expression (2) below, $$0.3 \leq h/r \leq 0.6 \quad (2)$$

is satisfied.

Where settings of around r=70 μm and h=35 μm are made as conditions satisfying expressions (1) and (2), effects of easy processing to form the reflectors 151 and enabling provision of a sufficiently high function that diffuses incoming light as a light diffusion portion.

Note that where h/r is smaller than the lower limit in expression (2), the diffusion function is lowered. On the other hand, where h/r is large beyond the upper limit in expression (2), a ratio of light confined inside the reflectors 151 increases and an amount of light exiting from an exit surface 131 decreases.

According to the present modification, light falling on the back face of the annular portion 132 of the light-guiding body 112 can be scattered and made to efficiently exit from the exit surface 131. Other operations and effects of the present modification are similar to those of the fourth embodiment. Note that the surface of the back face of the annular portion 132 on which the reflectors 151 are provided may be mirror-coated by the mirror coating portion 142 illustrated in FIG. 22A.

Figure 24:
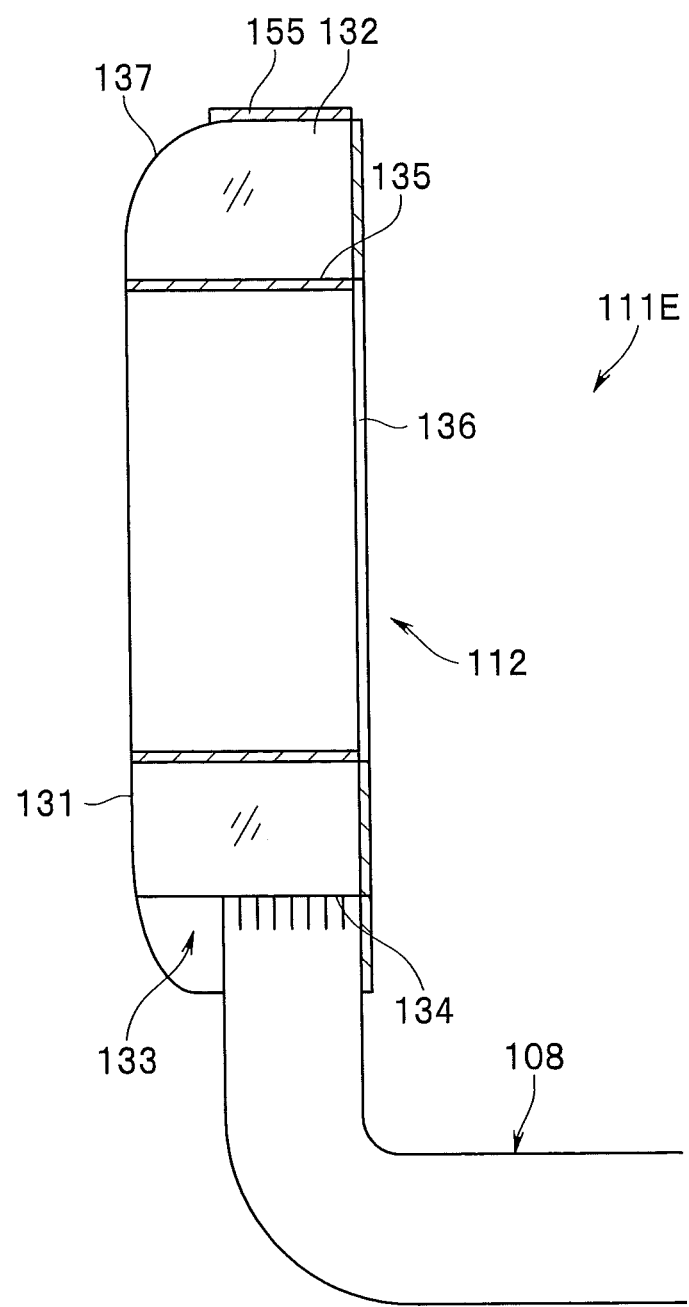
FIG. 24 is a cross-sectional side view of an illumination apparatus for an endoscope in a fifth modification of the fourth embodiment.

Also, as in an illumination apparatus 111E for an endoscope according to a fifth modification, which is illustrated in FIG. 24, a light scattering/light diffusion portion 155 that scatters or diffuses illuminating light entering from the inside of an annular portion 132 to the inside of the annular portion 132 may be provided on a part of an outer circumferential face of the annular portion 132.

In the example illustrated in FIG. 24, in the illumination apparatus 111 for an endoscope according to the fourth embodiment, the light scattering/light diffusion portion 155 is provided not on the entire outer circumferential face of the annular portion 132 but on the outer circumferential face excluding a part of the outer circumferential face close to the exit surface 131 in which a curved surface 137 is formed. Note that the light scattering/light diffusion portion 155 may be provided on the outer circumferential face except the part in the vicinity of the exit surface 131 or the outer circumferential face close to the back face.

As described above, provision of the light scattering/light diffusion portion 155 enables illuminating light falling on the outer circumferential face of the annular portion 132 at an angle close to a right angle, which would exit to the outside of the outer circumferential face without being reflected to the inside of the annular portion 132 by the outer circumferential face (in this case, illuminating light deviated from the illumination range) where the light scattering/light diffusion portion 155 is not provided, to be scattered or diffused to the inside of the annular portion 132.

Consequently, an amount of illuminating light exiting to the illumination range can be increased. Other operations and effects of the present modification are similar to those of the fourth embodiment.

(Fifth Embodiment)

Figure 25:
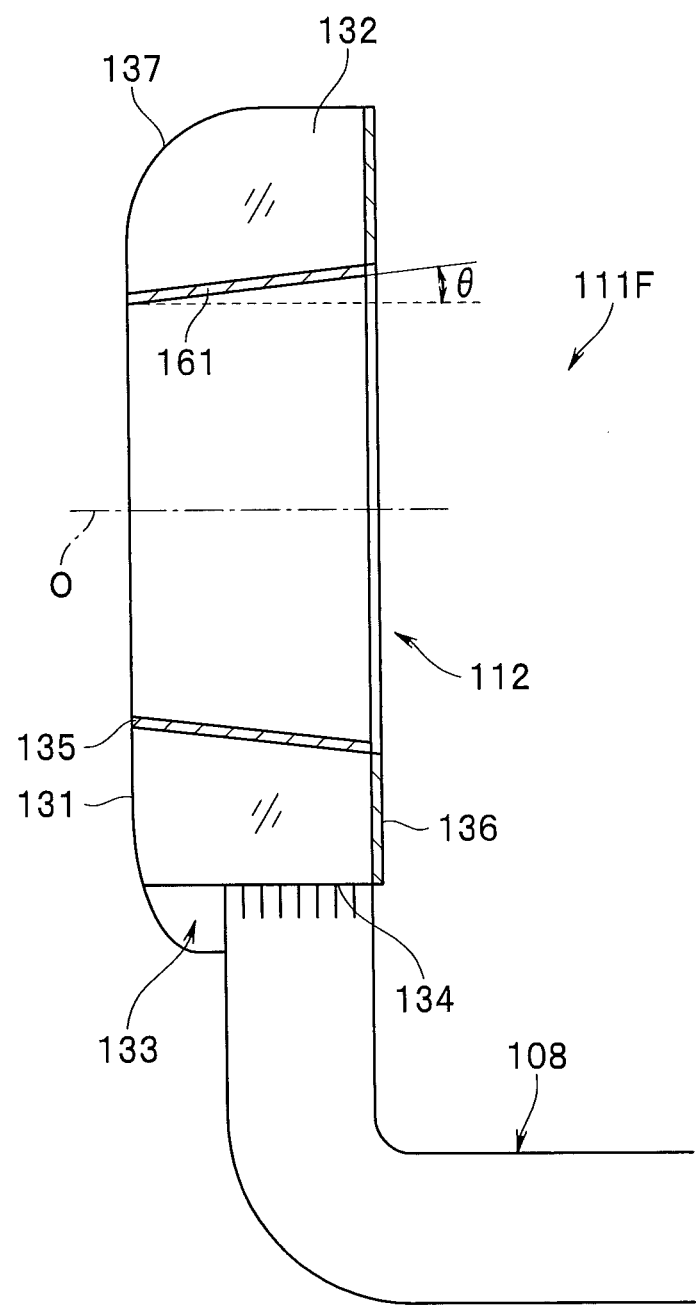
FIG. 25 is a cross-sectional side view illustrating a configuration of an illumination apparatus for an endoscope according to a fifth embodiment of the present invention.

Next, an illumination apparatus 111F for an endoscope according to a fifth embodiment of the present invention will be described with reference to FIG. 25. In the illumination apparatus 111F for an endoscope according to the present embodiment, for example, a change is made to the shape of the inner circumferential face of the annular portion 132 of the illumination apparatus 111 for an endoscope according to the fourth embodiment.

In the present embodiment, an inner circumferential face of an annular portion 132 includes a conical surface 161 having a diameter increasing from the exit surface 131 side to the back side opposite to an exit direction along a center axis O of the annular portion 132 to have a tapered shape. On a surface of the conical surface 161, a reflective material 135 is formed as in the case of the fourth embodiment.

As described above, the inner circumferential face is made to have the shape of the conical surface 161, enabling a function that reflects illuminating light falling on the inner circumferential face from the inside of the annular portion 132 so as to be guided toward the exit surface 131 can be enhanced relative to a case where no conical surface 161 is formed.

Note that in the case of the present embodiment, an angle θ formed by a direction parallel to the center axis O of the annular portion 132 and the conical surface 161 is set to around 1°≤θ≤10°. The rest of the configuration is similar to that of the fourth embodiment.

Next, an operation of the present embodiment will be described with reference to FIG. 26A. As indicated by arrows in FIG. 26A, illuminating light entering from a light guide 108 perpendicularly to the center axis O of the annular portion 132 falls on the inner circumferential face, or is guided along an annularity of the annular portion 132 and reflected by an outer circumferential face at a top face position and falls on the inner circumferential face.

Since the inner circumferential face is inclined toward the back side so as to have an increasing diameter, as indicated by arrows, illuminating light reflected by the reflective material 135 is guided toward the exit surface and exits from the exit surface 131.

Figure 26A:
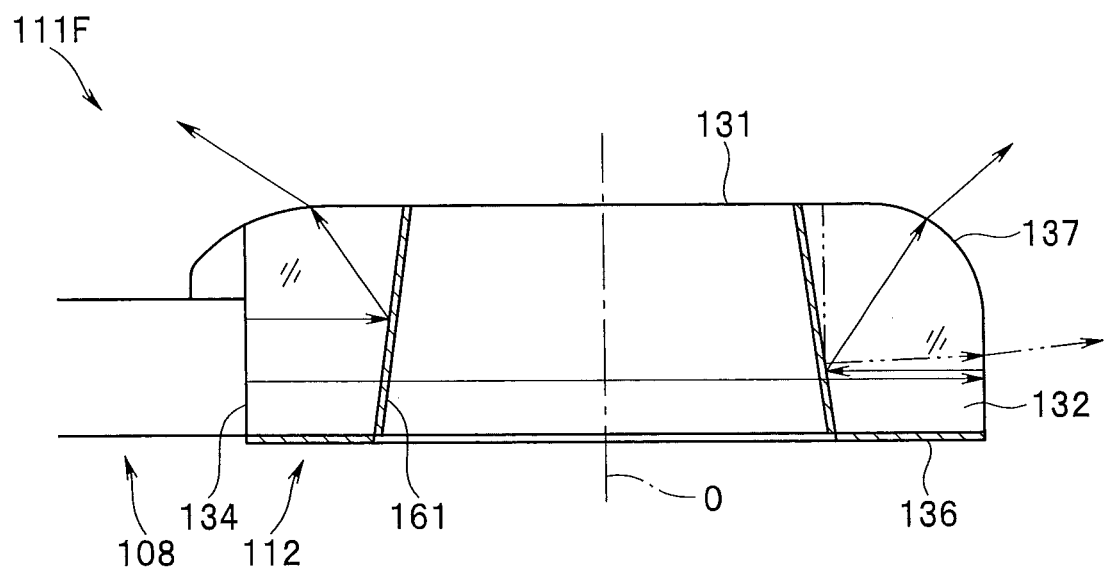
FIG. 26A is a diagram illustrating a manner in which illuminating light is guided in the fifth embodiment.

On the other hand, in FIG. 26A, in the case of an inner circumferential face having no tapered shape as indicated by an alternate long and two short dashes line, illuminating light falling on the inner circumferential face is reflected to the outer circumferential face, and thus, a ratio of light exiting from the outer circumferential face increases and an amount of light guided to the exit surface 131 decreases compared to the case of the present embodiment.

Figure 26B:
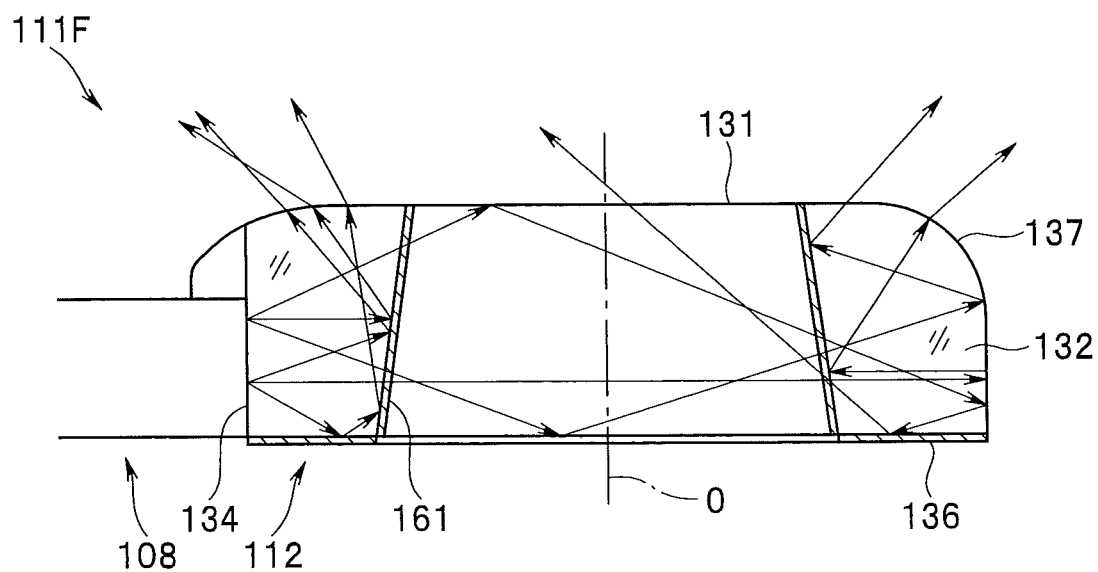
FIG. 26B is a diagram illustrating a manner in which illuminating light is guided in more detail relative to the case of FIG. 26A.

FIG. 26B illustrates a manner in which illuminating light in directions other than the direction perpendicular to the center axis O in the case of FIG. 26A is guided.

According to the present embodiment, illuminating light entering the inside of the annular portion 132 of the light-guiding body 112 can efficiently be guided to the exit surface 131 side to exit. Other operations and effects of the present embodiment are similar to those of the fourth embodiment.

Figure 27:
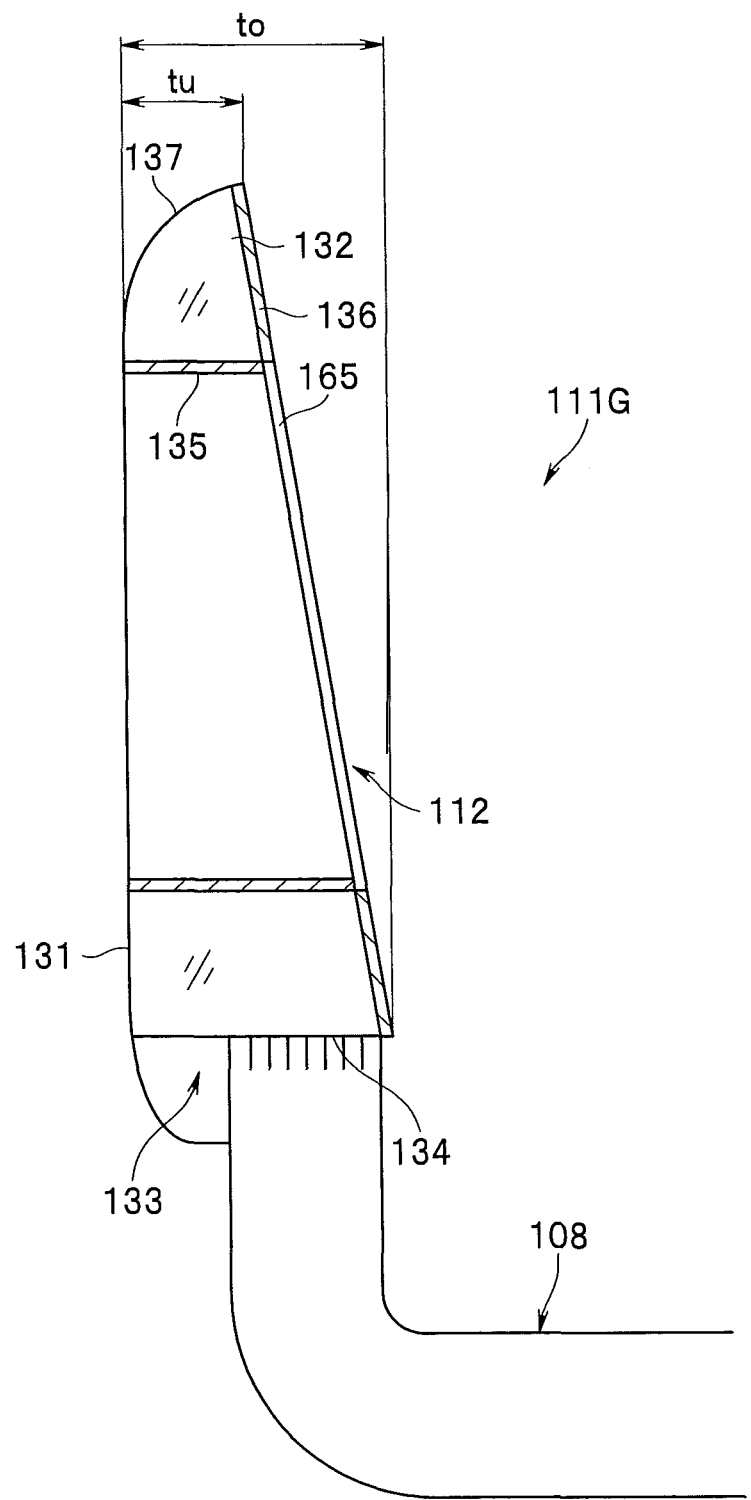
FIG. 27 is a cross-sectional view of an illumination apparatus for an endoscope according to a first modification of the fifth embodiment.

FIG. 27 illustrates a cross-sectional side view of an illumination apparatus 111G for an endoscope according to a first modification of the fifth embodiment. While the illumination apparatus 111F for an endoscope according to the fifth embodiment is one resulting from a change being made to the shape of the inner circumferential face of the annular portion 132 in the fourth embodiment, the illumination apparatus 111G for an endoscope according to the present modification has a structure with the back face of the annular portion 132 modified.

As illustrated in FIG. 27, in the present modification, a back face of an annular portion 132 of a light-guiding body 112 is inclined relative to a direction parallel to an exit surface 131 so that a thickness of the annular portion 132 decreases toward the far side (farther away) from an incident end face 134 on which illuminating light falls from a light guide 108.

In other words, the back face is inclined so that if a thickness between the exit surface 131 and the back face of the annular portion 132 is to at an incident end face 134 at a lower end of the annular portion 132, the thickness to decreases toward the upper side farther away from the incident end face 134, and at a position of a top end, the thickness is to (to>tu), which is the smallest, to form an inclined back face 165.

Note that on a surface of the inclined back face 165, a light diffusion portion 136, which has been described in the fourth embodiment, is provided. The rest of the configuration is similar to that of the fourth embodiment. Note that although the present modification has been described in terms of a case where the present modification is applied to the fourth embodiment, the present modification may be applied to a case where the inner circumferential face of the annular portion 132 is formed in a tapered shape as in the fifth embodiment.

Figure 28A:
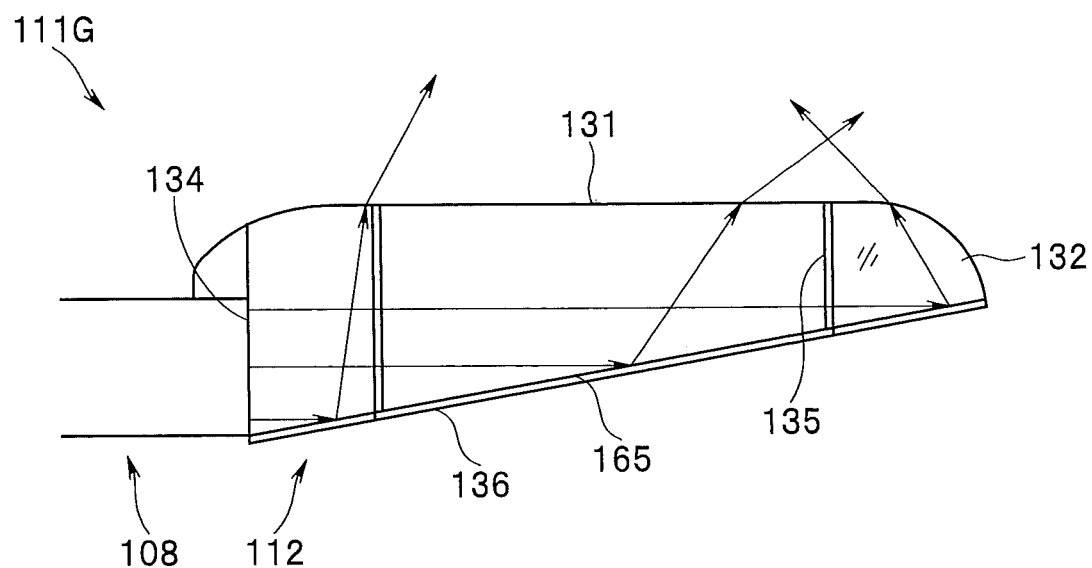
FIG. 28A is a diagram illustrating a manner in which illuminating light is guided in a second modification of the fifth embodiment.
Figure 28B:
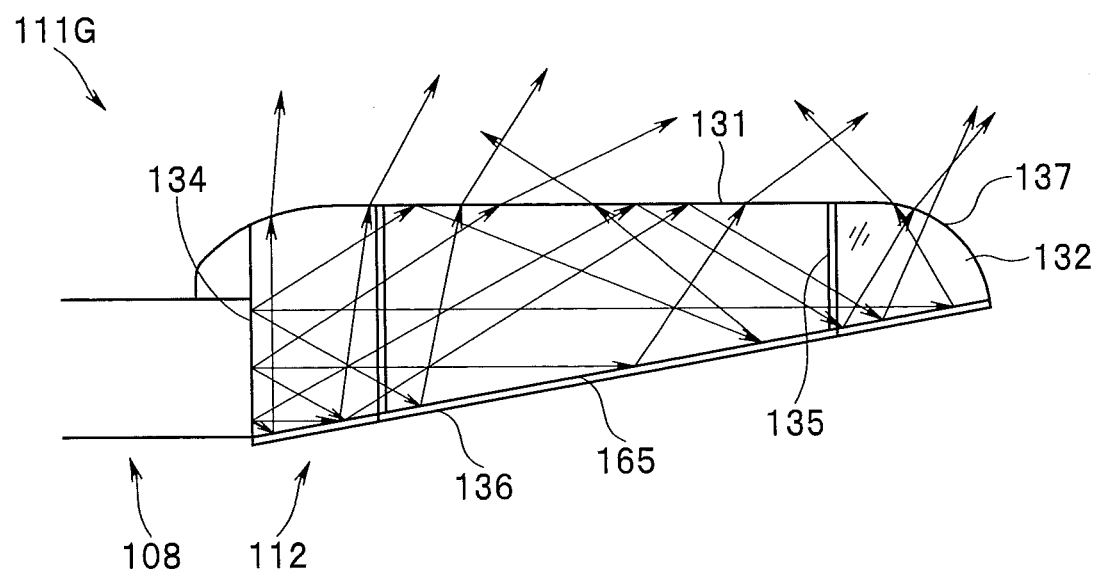
FIG. 28B is a diagram illustrating a manner in which illuminating light is guided in more detail relative to the case of FIG. 28A.

FIG. 28A illustrates a manner in which illuminating light entering in parallel to an exit surface 131 from a light guide 108 is diffused by a light diffusion portion 136 provided on a surface of an inclined back face 165. Also, FIG. 28B illustrates a manner in which illuminating light entering in directions other than a direction parallel to the exit surface 131 is diffused by the light diffusion portion 136 on the inclined back face 165 in addition to the case of FIG. 28A.

As described above, in the present modification, formation of the inclined back face 165 resulting from the back face being inclined enables an increase in illuminating light falling on a part of the back face far from the incident end face 134 relative to a case where no inclined back face 165 is formed, in terms of probability (statistic), and diffusion by the light diffusion portion 136 at the back face part enables an increase in illuminating light exiting from the exit surface 131.

In the above-described embodiments (including the modifications), illuminating light from the light guide 108 enters the annular portion 132 in a direction perpendicular to the center axis of the annular portion 132 of the light-guiding body 112.

On the other hand, as in the below-described modification, a configuration in which a direction of illuminating light entering from the light guide 108 forms an angle α that is smaller than 90°, with the center axis O of the annular portion 132a and the illuminating light enters toward the back face opposite to the exit surface 131 of the annular portion 132 may be employed.

Figure 29:
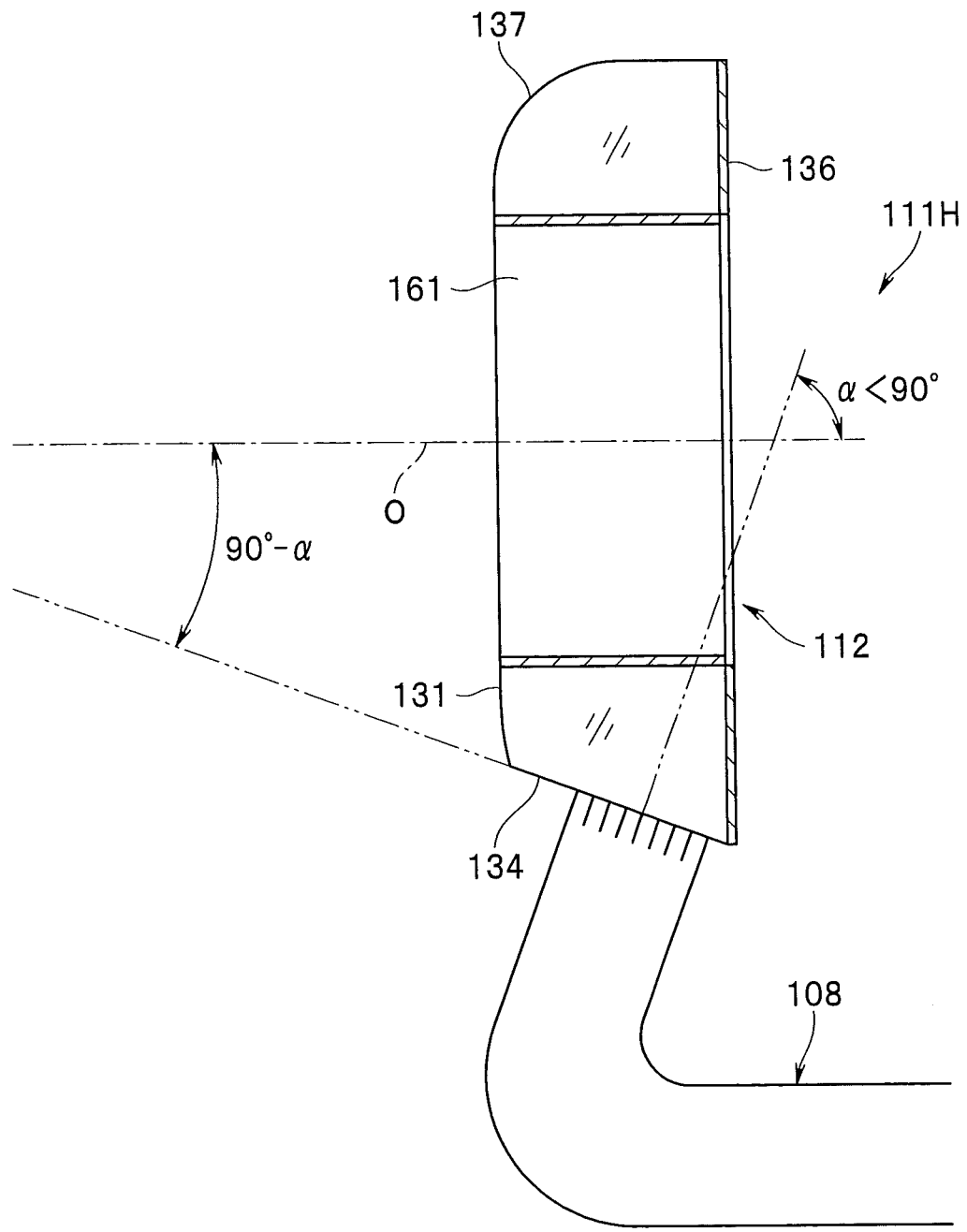
FIG. 29 is a side view of an illumination apparatus for an endoscope according to a third modification of the fifth embodiment.

FIG. 29 is a cross-sectional side view of an illumination apparatus 111H for an endoscope according to a second modification of the fifth embodiment. Note that a front view of the present modification is almost similar to FIG. 20A.

As illustrated in FIG. 29, a part in the vicinity of a distal end of a light guide 108 is flexed at an angle equal or exceeding 90° and each of distal end faces thereof forms an angle of 90°-α with a center axis O.

Likewise, each of incident end faces 134 that are in contact with the respective end faces of the distal end of the light guide 108 forms an angle of 90°-α with the center axis O. Also, on a back face of an annular portion 132, a light diffusion portion 136 including, e.g., a rough surface is formed. The rest of the configuration is similar to that of the fourth embodiment.

According to the present modification, as in the first modification, a ratio of illuminating light entering the inside of the annular portion 132 of the light-guiding body 112 from the end faces of the light guide 108 being guided to the light diffusion portion 136 on the back face of the annular portion 132. Accordingly, an efficiency of illuminating light exiting from an exit surface 131 to an illumination range that covers an observation range is enhanced. In other words, an amount of illuminating light exiting from the exit surface 131 can be increased without increasing a diameter of the light guide 108. Other effects of the present modification are similar to those of the fourth embodiment.

Figure 30:
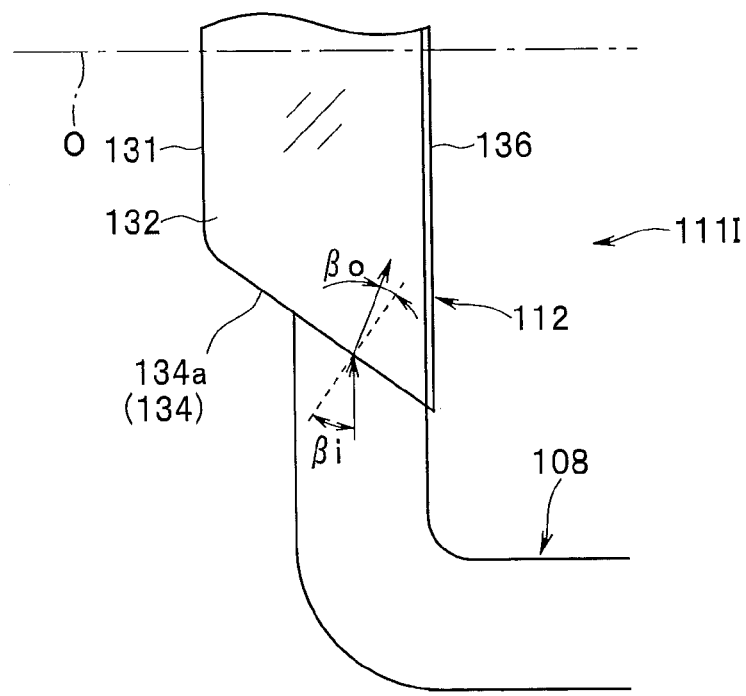
FIG. 30 is a diagram illustrating a part of an illumination apparatus for an endoscope according to a fourth modification of the fifth embodiment.

FIG. 30 illustrates a structure in the vicinity of incident end faces of an annular portion 132 of an illumination apparatus 111I for an endoscope according to a third modification.

In the present modification, the distal end side of the light guide 108 is flexed at an angle of 90° as in the cases of the fourth and fifth embodiments, end faces of the distal end are cut obliquely and incident end faces 134 of an annular portion 132 are inclined end faces 134a so that the incident end faces 134 are directed toward the back face relative to a direction perpendicular a center axis O of the annular portion 132.

Furthermore, a refractive index nd of a light-guiding body 112 included in the annular portion 132 is made to be larger than a refractive index n1 of the light guide 108.

Then, as illustrated in FIG. 30, illuminating light falling on the inclined end faces 134a forming the incident end faces 134 of the annular portion 132 from the distal end faces of the light guide 108 is made to enter after the illuminating light is flexed toward the back face at the refractive index nd larger than the refractive index n1 of the light guide 108.

In other words, where $\beta i$ is an angle of incidence on the inclined end faces 134a from the light guide 108 and $\beta o$ is an angle of exit to the inside of the annular portion 132 of the light-guiding body 112, $\beta i > \beta o$, and illuminating light entering the inside of the annular portion 132 is guided toward the light diffusion portion 136 on the back face. The present modification has operations and effects similar to those of the second modification of the present embodiment.

Figure 31:
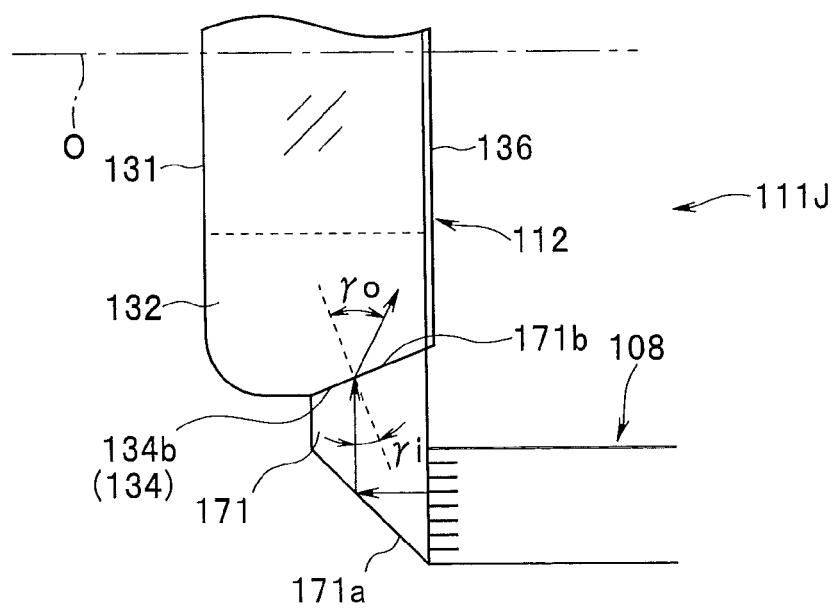
FIG. 31 is a diagram illustrating a part of an illumination apparatus for an endoscope according to a fifth modification of the fifth embodiment.

Note that as in an illumination apparatus 111J for an endoscope according to a fourth modification, which is illustrated in FIG. 31, a structure in which the distal end side of a light guide 108 is not flexed may be provided and a light-guiding member 171 may be arranged between end faces of a distal end thereof and incident end faces 134 of a light-guiding body 112. As illustrated in FIG. 31, incident end faces of the light-guiding member 171 contact the end faces of the distal end of the light guide 108, and illuminating light entering from the distal end faces of the light guide 108 is reflected at a right angle by a reflective surface 171a and guided to an exit end face 171b facing the reflective surface 171a.

In the present modification, also, the incident end faces 134 of the light-guiding body 112 are each set to have an inclined end face 134b forming an angle smaller than 90° with a plane perpendicular to a center axis O.

Also, a refractive index n1 of the light-guiding member 171 is made to be larger than a refractive index nd of the light-guiding body 112 (n1>nd). Accordingly, where $\gamma i$ is an angle of incidence from the light-guiding member 171 to the inclined end faces 134b and $\gamma o$ is an angle of exit to the inside of the annular portion 132 of the light-guiding body 112, $\gamma i < \gamma o$, and illuminating light entering the inside of the annular portion 132 is guided toward the light diffusion portion 136 on the back face.

The present modification has effects similar to those of the second modification.

Note that, e.g., embodiments formed by partially combining any of the above-described embodiments (including the modifications) also belong to the present invention. Furthermore, in the above-described embodiments and the like, for example, instead of the light scattering/light diffusion portion 155 in FIG. 24 a reflective portion that reflects light may be provided. Furthermore, for example, instead of the reflective material 135 provided on the inner circumferential face of the annular portion 132 in FIG. 20B, a light scattering portion that scatters light may be provided.

Furthermore, although the above embodiments have been described in terms of a case where two incident end faces 134 are provided as an incident portion which illuminating light enters from the light guide 108, as in an illumination apparatus 111K for an endoscope, which is illustrated in FIG. 32, a configuration in which illuminating light falls on one incident end face 134 only may be employed.

As illustrated in FIG. 32, the light guide 108 is slightly flexed without a part in the vicinity of a distal end thereof being branched into a Y-shape, and an end face thereof contacts the incident end face 134, allowing illuminating light from the light guide 108 to perpendicularly enter the incident end face 134.

Furthermore, on a surface of an end face 134' of the annular portion 132 of the light-guiding body 112, which is not used as an incident end face 134, a reflective portion 181 that reflects light is provided to reflect light falling on the end face 134' from the inside of the annular portion 132 (so as to be returned) to the inside of the annular portion 132. Note that instead of the reflective portion 181, a light scattering portion or a light diffusion portion may be provided. The rest of the configuration is similar to, for example, that of the fourth embodiment.

The present illumination apparatus 111K for an endoscope have effects substantially similar to those of the fourth embodiment. Although the description has been provided in terms of a case where a configuration including only one incident end face 134 is applied to the fourth embodiment, the configuration may be applied to any of the other modifications and the fifth embodiment and the like. For example, as indicated by the alternate long and two short dashes line in FIG. 32, a reflective portion 182 may be provided on an outer circumferential face of the annular portion 132. In this case, although the reflective portion 182 may be provided on the entire outer circumferential face, as illustrated in FIG. 24, the reflective portion 182 may be provided on the entire outer circumferential face excluding a part in the vicinity of the exit surface 131 provided on the curved surface 137 or a part of the outer circumferential face close to the back face. The reflective portion 182 suppresses illuminating light falling on the outer circumferential face from the inside of the annular portion 132 exiting to the outside of the outer circumferential face even in the case of a small incident angle, enabling an increase in amount of illuminating light exiting from the exit surface 131. Note that instead of the reflective portion 182, a light scattering portion or a light diffusion portion may be provided.

Note that embodiments and like formed by partially combining any of the above-described embodiments and modifications and the like also belong to the present invention.

What is claimed is:

1. An illumination apparatus for an endoscope, the illumination apparatus guiding externally-entering light through a light-guiding member to a transparent light-guiding body including an annular portion having an annular shape, the annular portion including an inner circumferential face and an outer circumferential face, and making the light exit from the annular portion as illuminating light, wherein the light-guiding body comprises:

a notch portion provided by cutting out an outer circumference of the annular portion, the notch portion configured to include two incident portions as two surfaces facing two exit surfaces which are distal end faces of the light-guiding member having a distal end side branched in a V-shape, the two surfaces having shapes on which light from the two exit surfaces falls perpendicularly, wherein the two incident portions are surfaces by cutting so as to form two lines extending perpendicularly to first and second lines respectively extending from two points on a circumference of a circle in a cross-section of the annular portion, from the outer circumferential face toward the inner circumference side of the annular portion, and the notch portion of the light-guiding body has a cross section of a shape formed by cutting the annular portion so as to cut out a part of an outer shape which is formed by a circle in a cross section of the annular portion and the first and second lines extending to be tangent to the circle at the two points on the circumference of the circle, in directions of crossing the two lines extending perpendicularly to the first and second lines and in such a manner that the annular shape is not disconnected.

2. The illumination apparatus for an endoscope according to claim 1, wherein a reflective portion arranged on at least a side of the inner circumferential face of the annular portion on which the notch portion is provided, the reflective portion reflecting the illuminating light entering the light-guiding body to an inside of the annular portion, is further provided.

3. The illumination apparatus for an endoscope according to claim 2, wherein the reflective portion includes a reflective material including a surface that reflects the illuminating light falling on the inner circumferential face from the inside of the annular portion toward the inside of the annular portion.

4. The illumination apparatus for an endoscope according to claim 1, wherein the annular portion includes a light diffusion portion that diffuses the entering illuminating light in a direction having an angle relative to a direction perpendicular to an annular surface of the annular portion and makes the illuminating light exit.

5. The illumination apparatus for an endoscope according to claim 4, wherein the light diffusion portion is provided on at least a part of an exit surface of the annular portion.

6. The illumination apparatus for an endoscope according to claim 1, wherein the annular portion includes a conical inner circumferential face that expands from a surface that has the annular shape and makes the illuminating light exit to a back side opposite to the exit surface so as to have a tapered shape.

7. The illumination apparatus for an endoscope according to claim 1, wherein a thickness of the annular portion decreases in a direction farther away from the incident portion for the illuminating light.

8. The illumination apparatus for an endoscope according to claim 1, wherein the light-guiding body includes a light reflective surface formed on the inner circumferential face and a light transmissive surface formed on the outer circumferential face.

9. The illumination apparatus for an endoscope according to claim 1, comprising a wedge-shaped reflective surface at a position on an upper side of the light-guiding body in order to make light guided inside the light-guiding body exit forward of the annular portion, the reflective surface being formed by cutting out a part of the annular portion from a back side opposite to a front face of the annular portion toward the front side into a wedge shape.

10. The illumination apparatus for an endoscope according to claim 1, wherein a light diffusion portion that reflects light in a scattered manner is provided on an exit surface of the annular portion opposite to a surface that has the annular shape and makes the illuminating light exit.

11. The illumination apparatus for an endoscope according to claim 10, wherein the light diffusion portion includes a roughened surface provided on the surface of the annular portion opposite to the exit surface that has the annular shape and makes the illuminating light exit.

12. The illumination apparatus for an endoscope according to claim 1, wherein in the light-guiding body, a light reflective surface is formed on each of the inner circumferential face and the outer circumferential face.

13. An endoscope comprising, at a distal end portion of an insertion portion to be inserted into a body cavity, a forward-viewing observation window in which an objective lens for forward-viewing is provided, the forward-viewing observation window having a observation field of view for forward-viewing that is a forward side in an axis direction of the insertion portion, the illumination apparatus for an endoscope according to claim 1 arranged in an illuminating window formed on an outer circumferential side of the forward-viewing observation window, the illumination apparatus guiding light entering a lower side of the observation field of view for forward viewing to make the illuminating light exit, a light guide provided in the insertion portion of the endoscope, the light guide allowing light guided from outside to enter the illumination apparatus for an endoscope, and a support portion that supports the light guide to be allowed to guide the light with a distal end face of the light guide facing the illumination apparatus for an endoscope.

14. The endoscope according to claim 13, further comprising:

a side-viewing observation window on a back side of the forward-viewing observation window in which the objective lens for forward-viewing is provided, the side-viewing observation window having an observation field of view for side-viewing that is a lateral side perpendicular to the axis direction of the insertion portion, and a side-viewing illuminating window that makes side-viewing illuminating light exit to the observation field of view for side-viewing.

15. The endoscope according to claim 14, wherein the light-guiding body is arranged so that a front face thereof is exposed at an illumination window formed on an outer circumferential side of the forward-viewing illuminating window so as to make illuminating light exit to the observation field of view for forward-viewing and an outer circumferential face thereof is exposed at the side-viewing illuminating window, and the light-guiding body performs both forward-viewing illumination and side-viewing illumination.

16. The endoscope according to claim 15, wherein an objective lens system that forms an object image for forward-viewing on a circular region at a center of an image pickup surface of an image pickup device arranged in the distal end portion via the objective lens for forward-viewing forms an object image for side-viewing in a substantially annular region outside the circle region in the image pickup surface of the image pickup device via the objective lens for side-viewing concentrically to the object image for forward-viewing.

17. The endoscope according to claim 14, wherein a second light-guiding body is arranged in the side-viewing illuminating window, the second light-guiding body including an annular shape different from the annular shape of the light-guiding body arranged in an illumination window formed on an outer circumferential side of the forward-viewing illuminating window, and a second light exit portion that makes light exit so as to enter a second incident portion formed by cutting an outer circumferential part of the second light-guiding body corresponding to a lower side of the observation field of view for forward-viewing is provided.

18. The endoscope according to claim 17, wherein the second light-guiding body includes the second incident portion formed by cutting out a part of an annular shape having a predetermined inner diameter and a predetermined outer diameter, and includes a light reflective surface formed on the inner circumferential face, a light transmissive surface formed on the outer circumferential face, a reflective surface that provides reflection in a scattered manner on each of a front face and a back face, and a reflective surface that reflects light to the outer circumferential face side at a position on an upper side opposite to a position of the second incident portion of the second light-guiding body, the reflective surface being formed by cutting out a part of the second light-guiding body from the inner circumferential face toward the outer circumferential face into a wedge shape.

\* \* \* \* \*